(12) United States Patent
Orcutt et al.

(10) Patent No.: US 10,514,504 B2
(45) Date of Patent: Dec. 24, 2019

(54) WAVEGUIDE FORMATION USING CMOS FABRICATION TECHNIQUES

(71) Applicant: Massachusetts Institute of Technology, Cambridge, MA (US)

(72) Inventors: Jason Scott Orcutt, Katonah, NY (US); Karan Kartik Mehta, Cambridge, MA (US); Rajeev Jagga Ram, Arlington, MA (US); Amir Hossein Atabaki, Medford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/902,455

(22) Filed: Feb. 22, 2018

(65) Prior Publication Data
US 2018/0180811 A1    Jun. 28, 2018

Related U.S. Application Data

(62) Division of application No. 15/365,548, filed on Nov. 30, 2016, now Pat. No. 9,946,022, which is a division
(Continued)

(51) Int. Cl.
*G02B 6/12*    (2006.01)
*G02B 6/136*    (2006.01)
(Continued)

(52) U.S. Cl.
CPC ............. *G02B 6/136* (2013.01); *G02B 6/122* (2013.01); *G02B 6/12004* (2013.01);
(Continued)

(58) Field of Classification Search
None
See application file for complete search history.

(56) References Cited

U.S. PATENT DOCUMENTS 5,559,912 A * 9/1996 Agahi ................ G02B 6/12007
385/131
6,775,453 B1    8/2004 Hornbeck et al.
(Continued)

OTHER PUBLICATIONS

Bogaerts et al., "Nanophotonic waveguides in Silcon-on-Insulator Fabricated with CMOS Technology", Journal of Lightwave Technology, vol. 23, No. 1, Jan. 2005, pp. 401-412.
(Continued)

*Primary Examiner* — Michael Stahl
(74) *Attorney, Agent, or Firm* — Smith Baluch LLP

(57) ABSTRACT

Conventional approaches to integrating waveguides within standard electronic processes typically involve using a dielectric layer, such as polysilicon, single-crystalline silicon, or silicon nitride, within the in-foundry process or depositing and patterning a dielectric layer in the backend as a post-foundry process. In the present approach, the backend of the silicon handle is etched away after in-foundry processing to expose voids or trenches defined using standard in-foundry processing (e.g., complementary metal-oxide-semiconductor (CMOS) processing). Depositing dielectric material into a void or trench yields an optical waveguide integrated within the front-end of the wafer. For example, a shallow trench isolation (STI) layer formed in-foundry may serve as a high-resolution patterning waveguide template in a damascene process within the front end of a die or wafer. Filling the trench with a high-index dielectric material yields a waveguide that can guide visible and/or infrared light, depending on the waveguide's dimensions and refractive index contrast.

16 Claims, 26 Drawing Sheets

Related U.S. Application Data of application No. 14/520,893, filed on Oct. 22, 2014, now Pat. No. 9,529,150.

(60) Provisional application No. 61/894,062, filed on Oct. 22, 2013.

(51) Int. Cl.
| | | |
|---|---|---|
| *G02B 6/132* | (2006.01) | |
| *G02B 6/122* | (2006.01) | |
| *G02F 1/01* | (2006.01) | |
| *G02F 1/025* | (2006.01) | |
| *G02B 6/30* | (2006.01) | |
| *G02F 1/015* | (2006.01) | |

(52) U.S. Cl.
CPC ........... *G02B 6/132* (2013.01); *G02F 1/0147* (2013.01); *G02F 1/025* (2013.01); *G02B 6/1225* (2013.01); *G02B 6/305* (2013.01); *G02B 2006/121* (2013.01); *G02B 2006/12061* (2013.01); *G02B 2006/12097* (2013.01); *G02B 2006/12107* (2013.01); *G02B 2006/12123* (2013.01); *G02F 2001/0151* (2013.01)

(56) References Cited

U.S. PATENT DOCUMENTS

| | | | |
|---|---|---|---|
| 7,001,788 B2 | 2/2006 | Leon et al. | |
| 7,010,208 B1 | 3/2006 | Gunn, III et al. | |
| 7,072,556 B1 | 7/2006 | Gunn, III et al. | |
| 7,082,247 B1 | 7/2006 | Gunn, III et al. | |
| 7,218,826 B1 | 5/2007 | Gunn, III et al. | |
| 7,298,941 B2 | 11/2007 | Palen et al. | |
| 7,354,840 B1 | 4/2008 | Kempf | |
| 7,471,866 B2 | 12/2008 | Dumais et al. | |
| 7,760,980 B2 | 7/2010 | West et al. | |
| 7,790,495 B2 | 9/2010 | Assefa et al. | |
| 7,920,770 B2 | 4/2011 | Holzwarth et al. | |
| 7,943,471 B1 | 5/2011 | Buller et al. | |
| 8,290,325 B2 | 10/2012 | Reshotko et al. | |
| 8,369,675 B2 | 2/2013 | Yanagisawa | |
| 8,437,585 B2 | 5/2013 | Na et al. | |
| 8,513,037 B2 | 8/2013 | Pomerene et al. | |
| 9,529,150 B2 | 12/2016 | Orcutt et al. | |
| 2003/0013304 A1 | 1/2003 | Deliwala | |
| 2003/0048970 A1* | 3/2003 | Cole | G01J 3/26 385/1 |
| 2003/0052082 A1 | 3/2003 | Khan et al. | |
| 2004/0190848 A1 | 9/2004 | Ide | |
| 2005/0053347 A1 | 3/2005 | West et al. | |
| 2005/0207691 A1 | 9/2005 | Keyser et al. | |
| 2005/0236619 A1 | 10/2005 | Patel et al. | |
| 2007/0053643 A1 | 3/2007 | West et al. | |
| 2007/0295686 A1 | 12/2007 | Mouli | |
| 2009/0134486 A1 | 5/2009 | Fujikata | |
| 2009/0136237 A1 | 5/2009 | Martini et al. | |
| 2009/0169149 A1 | 7/2009 | Block | |
| 2009/0180729 A1 | 7/2009 | Rasras | |
| 2009/0314763 A1 | 12/2009 | Chu et al. | |
| 2010/0092682 A1 | 4/2010 | Carothers | |
| 2010/0148221 A1 | 6/2010 | Yu et al. | |
| 2010/0322551 A1 | 12/2010 | Budd et al. | |
| 2011/0084047 A1 | 4/2011 | Yeo et al. | |
| 2012/0129302 A1 | 5/2012 | Assefa et al. | |
| 2013/0058606 A1 | 3/2013 | Thomson et al. | |
| 2013/0252359 A1 | 9/2013 | Mouli | |
| 2017/0146740 A1 | 5/2017 | Orcutt et al. | |

OTHER PUBLICATIONS

Dumon et al., "Towards foundry approach for silicon photonics: silicon photonics platform ePIXfab," Electronics Letters 45, 581-582 (2009).

Holzwarth et al., "Localized substrate removal technique enabling strong-con_nement microphotonics in bulk Si CMOS processes," in proceedings of the Conference on Lasers and Electro-Optics (San Jose, CA 2008).

Lee et al., "Back-end deposited silicon photonics for monolithic integration on CMOS," Journal of Selected Topics in Quantum Electronics 19, 8200207 (2012).

Notification of Transmittal of the International Search Report and the Written Opinion of the International Searching Authority, or the Declaration in related International Application No. PCT/US14/61728, filed Oct. 22, 2014, 10 pages.

Office Action dated Feb. 21, 2018 for Taiwanese Patent Application No. 103136530, 9 pages.

Orcutt et al., "Low-loss polysilicon waveguides fabricated in an emulated high-volume electronics process," Optics Express 20, 7243-7254 (2012).

Orcutt et al., "Nanophotonic integration in state-of-the-art CMOS foundries," Optics Express 19, 2335-2346 (2011).

Orcutt et al., "Open foundry platform for high-performance electronic-photonic integration," Optics Express 20, 12222-12232 (2012).

Piramanayagam et al., "Planarization of patterned recording media," Transactions on magnetics 46, 758-763 (2010).

Young et al., "Optical I/O technology for tera-scale computing," Journal of Solid State Circuits 45, 235-248 (2009).

Ex Parte Quayle Office Action dated Jun. 9, 2016 for U.S. Appl. No. 14/520,893, 6 pages.

Notice of Allowance dated Aug. 26, 2016 for U.S. Appl. No. 14/520,893, 6 pages.

Notice of Allowance dated Jan. 9, 2018 for U.S. Appl. No. 15/365,548, 7 pages.

\* cited by examiner

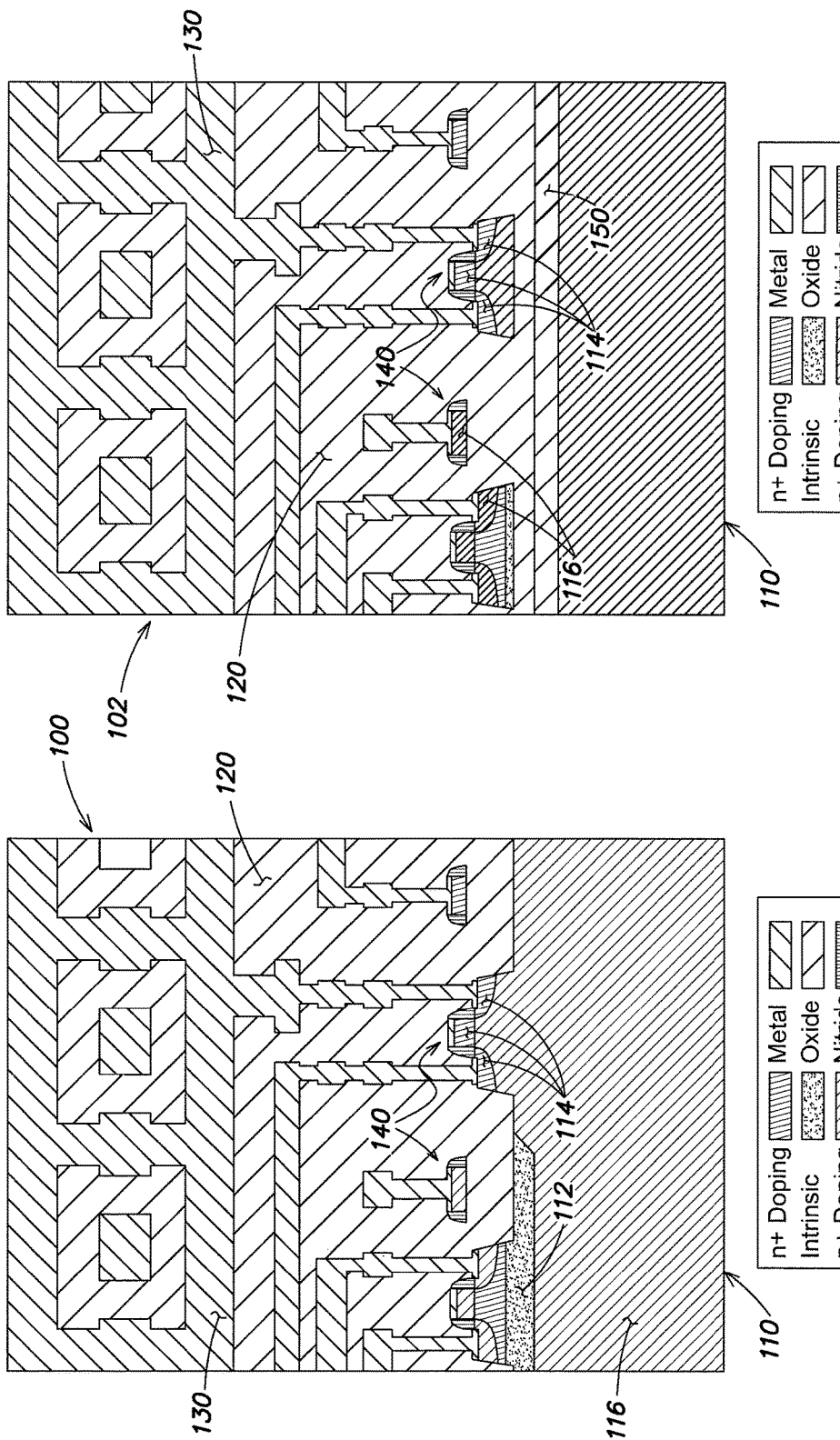

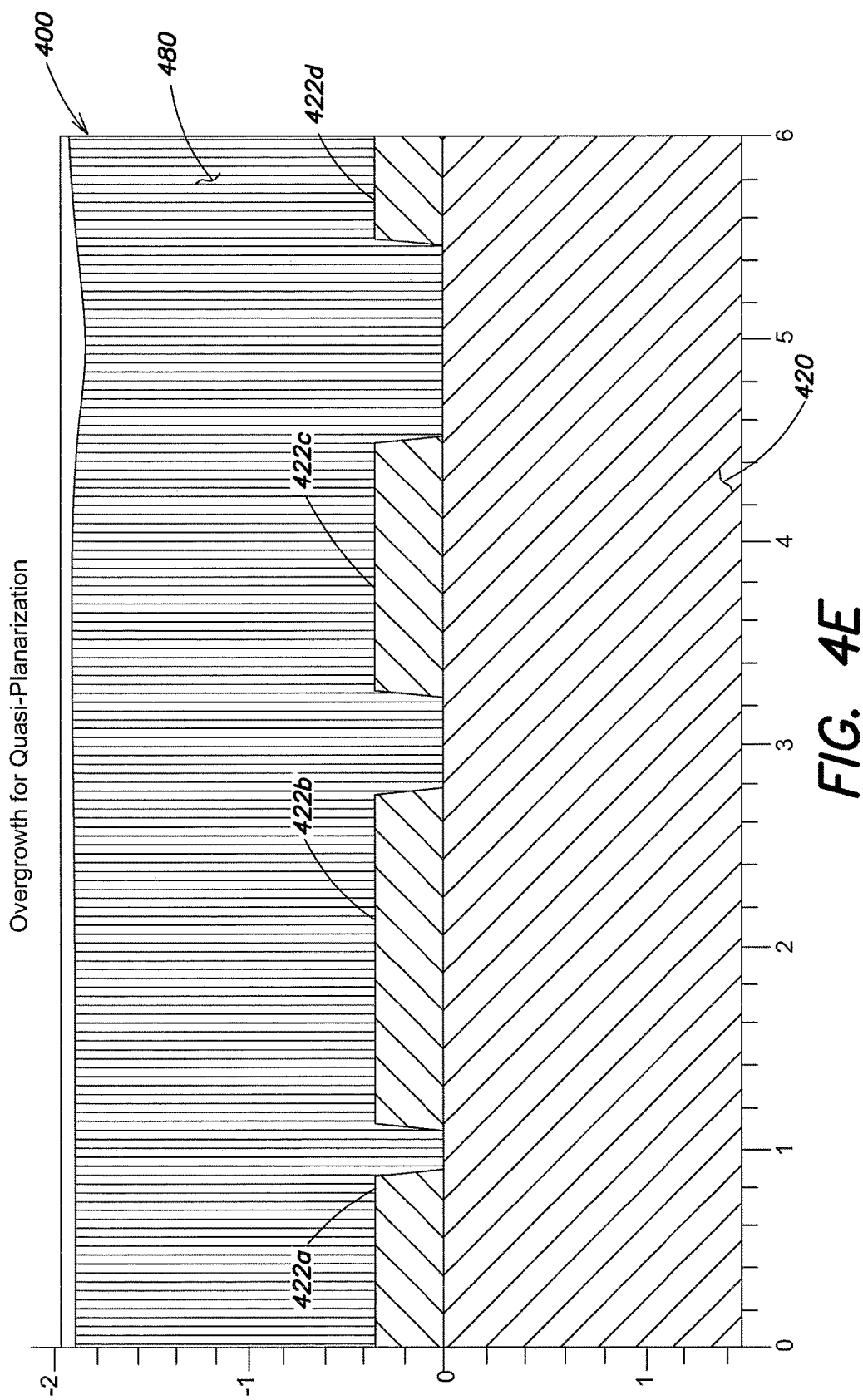

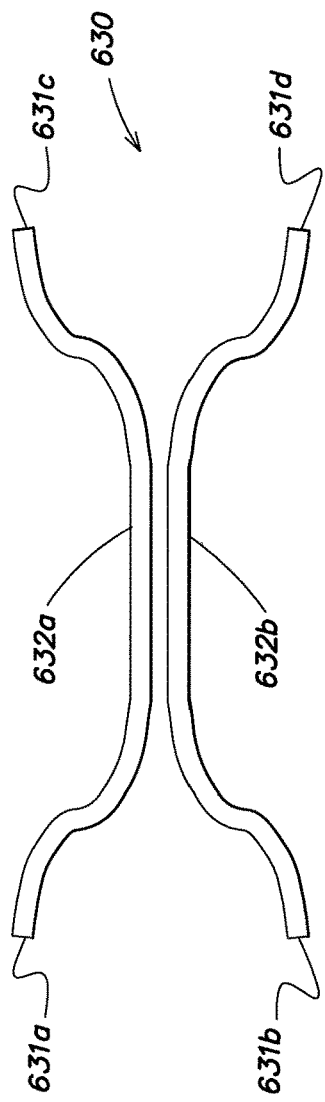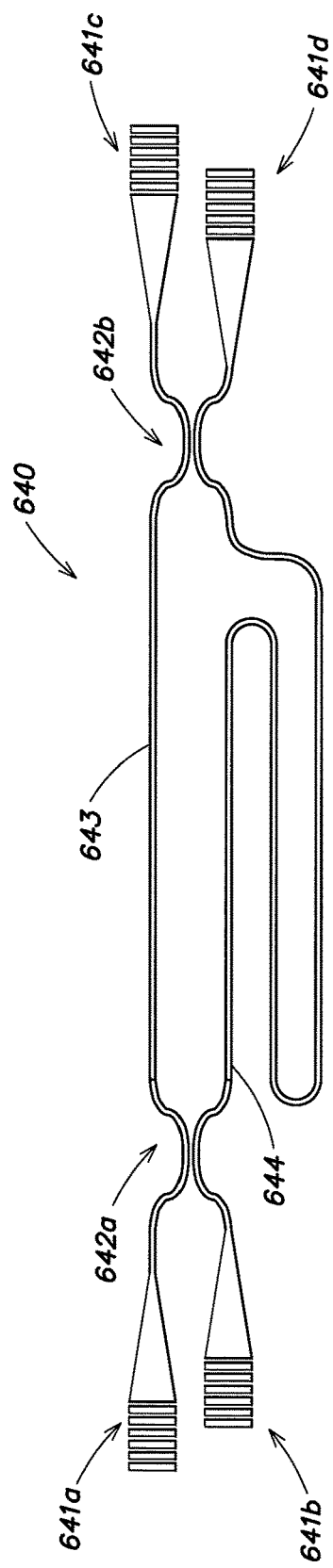

WAVEGUIDE FORMATION USING CMOS FABRICATION TECHNIQUES

CROSS-REFERENCE TO RELATED APPLICATION

This application is a divisional of U.S. application Ser. No. 15/365,548, now U.S. Pat. No. 9,946,022, entitled "Waveguide Formation Using CMOS Fabrication Techniques" and filed Nov. 30, 2016, which is a divisional of U.S. application Ser. No. 14/520,893, now U.S. Pat. No. 9,529,150, entitled "Waveguide Formation Using CMOS Fabrication Techniques" and filed Oct. 22, 2014, which in turn claims the benefit, under 35 U.S.C. § 119(e), of U.S. Application No. 61/894,062, entitled "Waveguide Formation Using CMOS Fabrication Techniques" and filed Oct. 22, 2013. Each of these applications is hereby incorporated herein by reference in its entirety.

GOVERNMENT SUPPORT

This invention was made with government support under Contract No. HR0011-11-C-0100 awarded by the Defense Advanced Research Projects Agency. The government has certain rights in the invention.

BACKGROUND

Complementary metal-oxide-semiconductor (CMOS) technology refers to both integrated circuits and the processes used to make integrated circuits. CMOS processes are generally carried out at CMOS foundries to make integrated circuits in silicon wafers or substrates. During a typical CMOS process, thousands to billions of field-effect transistors and other electronic devices can be formed in a single substrate by selectively etching, doping, and depositing different layers of metal, semiconductor, and dielectric materials on the substrate as well as etching and doping the substrate itself. Once the processing is complete, the substrate is then diced into individual chips, which can be packaged for use in electronic components.

In some cases, the integrated circuits include photonic components in addition to or instead of electronic components. Unfortunately, however, integrating optical waveguides into silicon substrates using standard CMOS processes has proven difficult for a number of reasons. For instance, although silicon transmits near-infrared light, it must be surrounded with a low-index material, such as silica (silicon dioxide) or another dielectric, to act as a waveguide. And silicon absorbs visible light, making it unsuitable for guiding visible light.

Unfortunately, conventional bulk CMOS manufacturing processes do not involve forming a single-crystalline silicon layer clad in a dielectric with a lower refractive index. To compensate for this lack, others have suggested depositing and patterning waveguides on top of the existing CMOS process layers instead of making changes to the conventional bulk CMOS manufacturing processes. But depositing and patterning waveguides on top of the existing CMOS process layers involves complicated processing and high resolution lithography on top of the complicated, non-planar film stack of the full electronic manufacturing process. Unfortunately, typical lithography steps in this part of the CMOS process are performed via I-line steppers to increase the depth of field, which may significantly reduce the available pattern resolution for the waveguide layer. Further, the additional steps required to deposit and pattern the waveguides may be expensive to develop and perform.

Besides the aforementioned fabrication complexity, depositing and patterning waveguides on top of the existing CMOS process layers also yields thick dielectric layers on top of the entire electronic chip. These thick dielectric layers degrade the chip's effective thermal conductance, decreasing its total allowable power dissipation and, as a result, limiting its maximum operation temperature. Additionally, the chip's power and communications typically pass through these thick dielectric layers, resulting in an undesired increase in the total inductance of the chip's power network and in the capacitance of the chip's signaling paths.

The dielectric layer can also be deposited underneath a silicon waveguide layer, e.g., as in silicon-on-insulator (SOI) waveguides. In a typical SOI waveguide, a layer of silicon is formed into a rib on top of a buried oxide layer (typically silicon dioxide) which in turn is on a silicon substrate. Although SOI rib waveguides are well known, they tend to be relatively expensive compared to conventional bulk CMOS devices; in some cases, an unprocessed SOI wafer can cost as much as a fully processed CMOS wafer. SOI CMOS processing is also available in only about 5% of CMOS foundries. And because silicon absorbs light at wavelengths below about 1100 nm, even SOI rib waveguides are unsuitable for guiding visible light.

SUMMARY

In view of the foregoing, the inventors have developed processes for integrating dielectric waveguides into CMOS devices without modifying the in-foundry process flow and with minimal post-foundry processing. These processes enable the formation of a variety of photonic platforms in bulk-CMOS devices. Some embodiments of these processes involve etching and/or planarization that results in waveguide geometries resembling silicon-on-insulator strip and rib waveguides. These photonic platforms may be used for sensing, chip-to-chip interconnections, and a variety of other Electronic Photonic Integrated Circuit (EPIC) needs. In addition, frameworks for designing and simulating exemplary integrated waveguides can be applied to other process flow waveguide formation cross-section analysis.

Embodiments of the present technology include methods of making at least one optical waveguide in a silicon substrate having a front side, a back side, and at least one ridge extending from the front side of the silicon substrate. A dielectric layer of first dielectric material is deposited on the front side of the silicon substrate over the ridge. In one example, the method includes a portion of the back side of the silicon substrate so as to form at least one trench in the dielectric layer via removal of the ridge. Depositing a waveguide core material, with a refractive index greater than that of the dielectric layer, into the trench forms a core of the optical waveguide.

Another embodiment includes a semiconductor device comprising a silicon substrate, a dielectric layer, and an optical waveguide. The silicon substrate has a front side and a back side and defines a recess extending through the silicon substrate from the back side of the silicon substrate to the front side of the silicon substrate. The dielectric layer comprises first dielectric material, having a first refractive index, disposed on the front side of the silicon substrate. The dielectric layer also defines a trench open to the recess defined by the silicon substrate. And the optical waveguide comprises a second dielectric material, having a second refractive index greater than the first refractive index, disposed within the trench.

Yet another embodiment includes a method of making at least one optical waveguide in a silicon substrate having a front side, a back side, and a first refractive index. Etching the front side of the silicon substrate defines a silicon ridge (e.g., with a width of 250 nm or less) on the front side of the silicon substrate. Next, a layer of dielectric material having a second refractive index lower than the first refractive index is deposited on the silicon ridge and on at least a portion of the front side of the silicon substrate adjacent to the ridge. Etching a portion of the back side of the silicon substrate exposes a portion of the silicon ridge through the silicon substrate from the back side of the silicon substrate to form a waveguide.

In some cases, the back side of the silicon substrate is etched by chemical-mechanical polishing. In other cases, a pn junction is defined in the silicon ridge, then the the back side of the silicon substrate is electro-chemically etched to the pn junction.

Another embodiment comprises a semiconductor device with a silicon substrate, a dielectric layer, and an optical waveguide. The silicon substrate has a front side, a back side, and a first refractive index, and defines a recess extending through the silicon substrate from the back side of the silicon substrate to the front side of the silicon substrate. The dielectric layer is made of first dielectric material, having a second refractive index lower than the first refractive index, disposed on the front side of the silicon substrate. The dielectric layer defines a trench (e.g., with a width of about 250 nm or less) open to the recess defined by the silicon substrate. And the optical waveguide comprises silicon disposed within the trench to form a waveguide core. In some example, a pn junction is formed in the silicon disposed within the trench.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1A shows across section of bulk CMOS electronics.

FIG. 1B shows a cross section of thin silicon-on-insulator (SOI) complementary metal-oxide-semiconductor (CMOS) electronics.

FIG. 2I shows a top view of the bulk CMOS device shown in FIG. 2H.

FIG. 4E shows a cross section of an overguide waveguide core layer for quasi-planarization.

FIG. 6C shows a directional coupler including a pair of waveguides that can be used to combine or divide light between different ports.

FIG. 6D shows a semiconductor device including a Mach-Zehnder interferometer and a waveguide fabricated using methods illustrated in FIG. 2A-2G.

DETAILED DESCRIPTION

Figure 2A:
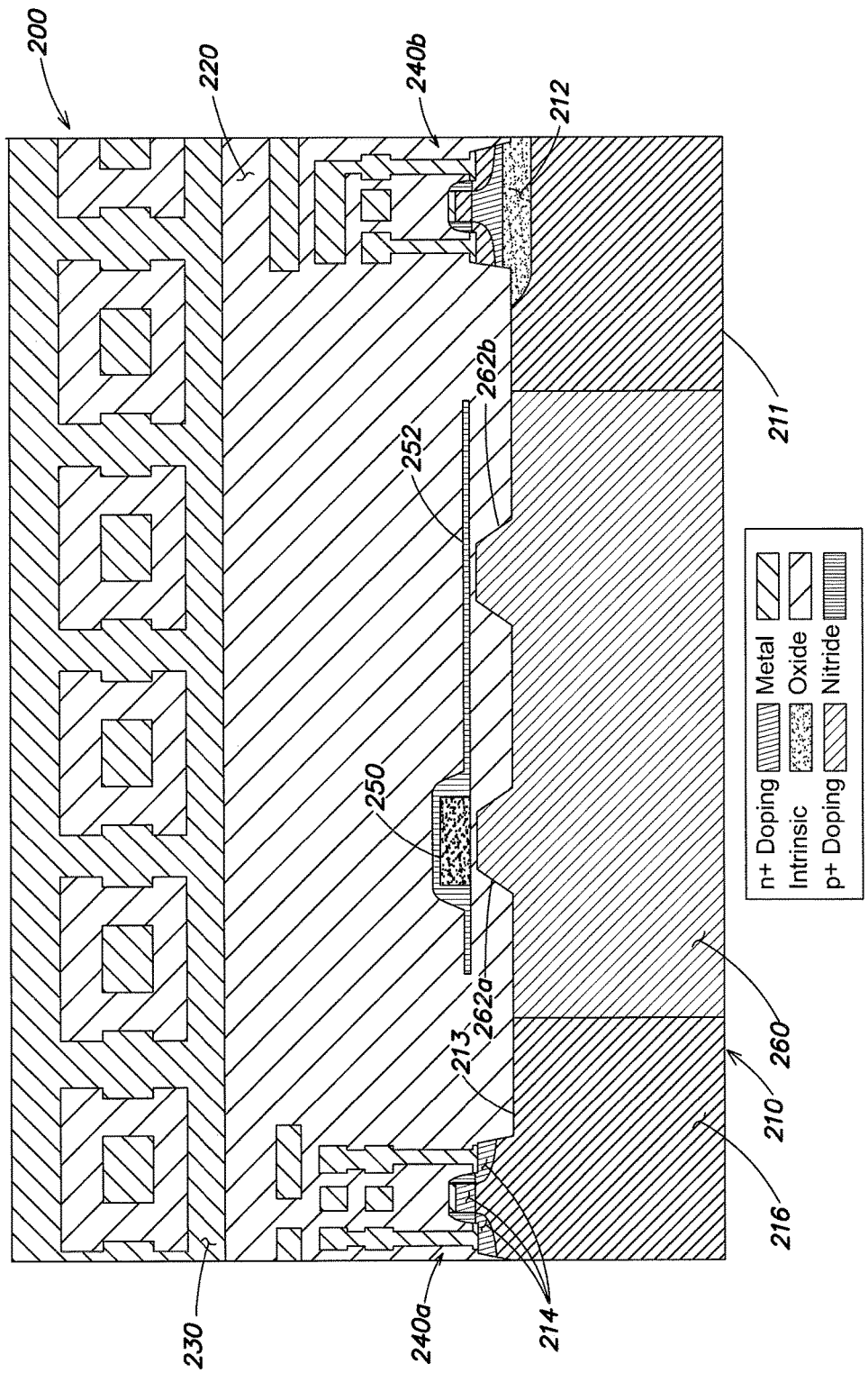
FIG. 2A shows a cross section of bulk CMOS electronics suitable waveguide formation via back-end processing.

Embodiments of the present technology include methods of forming an optical waveguide in a silicon substrate using a standard CMOS process flow without modifying the in-foundry portion of the CMOS process flow. In one example, the silicon substrate undergoes a conventional CMOS process in a CMOS foundry, including formation of any transistors or other electronic devices as well as the deposition of a layer of dielectric material (also known as a shallow trench isolation layer) on the front of the silicon wafer to prevent current from leaking between adjacent transistors. After in-foundry processing is complete, the silicon substrate is etched from the back to expose part of the dielectric layer deposited on the front of the silicon substrate. In other words, post-foundry processing involves etching a recess or hole all the way through the back of the silicon substrate. A narrow trench (e.g., with a width of 500 nm, 300 nm, 130 nm, or less) is formed in the surface of the dielectric layer exposed by etching away the silicon substrate. And an optical waveguide is formed by depositing a waveguide core material with a refractive index higher than that of the dielectric layer into the trench. The waveguide width (lateral thickness) is typically from 300 nm to a few microns (e.g., 300-500 nm for single-mode devices). In some cases, the waveguide width may be tapered to less than 100 nm. If desired, the waveguide core material can be patterned or clad in another material to further enhance confinement of the guided mode(s).

CMOS process technologies suitable for waveguide integration may involve high-precision (e.g., with feature sizes smaller than about 250 nm) photolithographic patterning of the active layer (inverse of the shallow-trench isolation regions), etching shallow-trench isolation sidewalls with high aspect ratios (e.g., steeper than 45°), and depositing reasonably thick shallow-trench isolation layers (e.g., with thicknesses of greater than or equal to about 200 nm). In some cases, waveguide integration may include locally blocking the silicidation of the active silicon, although this may be avoided through additional etching. These process constraints are generally found in bulk-CMOS logic processes having a feature size of 130 nm or below. Other CMOS processes, such as those used for 250 nm CMOS technology, often utilize local oxidation techniques to form the shallow-trench isolation which may result in unsuitably shallow sidewall angles. Additionally, 250 nm CMOS processes may not involve patterning suitable for photonic device integration.

Because the present methods involve post-foundry formation of the waveguide, they can be used without modifying the in-foundry portion of the CMOS process flow. More specifically, the technology disclosed herein does not require any in-foundry process changes and utilizes an existing high-resolution patterning step used for transistor definition to define the waveguide's path. In fact, a design for an exemplary photonic/electronic integrated circuit may be prepared in a database format specified by the foundry according to the foundry's particular design rules, including any non-waivable rules. And in some cases, aspects of an exemplary process may mirror the flow for using the active silicon layer (e.g., a floating transistor body) of a silicon-on-insulator CMOS process.

In certain examples of the present fabrication processes, the post-foundry process steps involve, at most, a single coarse photolithography step to define the recess. And the deposition, planarization, and etching can be carried out using well-established technologies that require minimal development or recurring costs. As a result, the present methods are compatible with the conventional CMOS processes used at least 95% of present CMOS foundries.

In addition, integrating the waveguide in the front end allows the photonics to easily couple to and be controlled by other electronic and photonic devices fabricated in the silicon transistor device plane using the standard CMOS process flow. For example, the waveguide(s) can be disposed in plane with the transistor body layer in the device front end as explained below. And since the waveguide is integrated within the front-end of the process, in the same plane as the electronics, it does not negatively affect the thermal or electrical properties of the electronics. Conversely, previous post-foundry backend integrated waveguides are typically physically distant (e.g., 5-10 μm) from the device front end in dielectric layers that increase the device inductance and capacitance and reduce heat dissipation.

Because an exemplary waveguide can be fabricated in the same plane as the silicon transistors, it can be positioned closer to single-crystalline silicon photodetectors or polycrystalline heaters formed in the device front end for use in the photonic platform. For example, the waveguide may be made of a material that transmit light at wavelengths normally absorbed by silicon (e.g., visible wavelengths) and butt-coupled to a high-efficiency silicon photodetector formed by source/drain and well doping implants in the transistor device plane.

Moreover, an exemplary waveguide can include a core made of any suitable material, including materials that are at least partially transparent at wavelength(s) absorbed by silicon. By choosing an appropriate core material, such as silicon nitride, silicon-rich silicon nitride, titanium oxide, tantalum oxide, zinc oxide, or aluminum oxide, the waveguide can be used to transmit light at one or more wavelengths between from about 400 nm to about 2000 nm—a region of the electromagnetic spectrum where silicon absorbs light. For instance, amorphous silicon, silicon nitride, silicon, and germanium could be used as the cores of infrared waveguides. And silicon nitride, aluminum oxide, aluminum nitride, silicon carbide, and zinc oxide could be used as cores of waveguides that guide visible or infrared light. These materials may be deposited by, for example, plasma enhanced chemical vapor deposition, sputtering, electron beam evaporation, atomic layer deposition, or other methods known in the art. Furthermore, polymers can also be included as the core waveguide material. Possible polymer materials can include photolime gel-based polymer, Ethylene glycol dimethylacrylate (EGDMA), poly(p-phenylene benzobisthiazole) (PBZT), dye-doped Poly(methyl methacrylate) (PMMA), polyphenylsilsesquioxanes (PPSQ), Perfluorocyclobutyl (PFCB), Benzocyclobutene (BCB), Polysiloxane, Chloro-fluorinated polyimides, acrylate monomers, epoxidized natural rubber (ENR), or other materials known in the art. In general, suitable polymers have an index that is slightly higher than silicon dioxide (e.g., n≈1.55-1.8) and/or have a high second- or third-order optical nonlinearity. The corresponding fabrication method can be, for example, spray coating, or spin coating followed by an etch-back step using oxygen plasma.

Applications of CMOS-Based Waveguide Formation

Examples of the waveguides and waveguide fabrication processes disclosed herein can be used in a wide variety of applications. For communication transceivers, simple low-loss photonic integration within bulk CMOS wafers opens up the approximately 92% of the manufacturing infrastructure that is incompatible with other techniques for high-performance photonic integration due to the lack of suitable single-crystalline silicon layer. This makes the waveguide integration in CMOS wafer backends a suitable choice for electronic-photonic application specific integrated circuits (ASICs) as well. For example, in electronic-photonic integrated circuits that operate at wavelengths where silicon is transparent (e.g., in the mid-infrared portion of the electromagnetic spectrum), an integrated nitride waveguide can be coupled to a high-performance integrated silicon photodetector.

Electronic-photonic integrated circuits with integrated waveguides may also be useful in integrated quantum optics, quantum computing, quantum communications, and quantum simulation. Leveraging existing CMOS processing techniques to provide optical, thermal, and electro-magnetic components in a single chip with on-board control and feedback circuitry could lead to a major increase in the number of interacting qubits for quantum computation, communication and simulation systems. For instance, integrated optical waveguides could be used in an integrated-photonic atom trap on a CMOS substrate that operates at visible wavelengths.

Photonic integrated circuits with integrated waveguides can also be used for integrated photonic biosensing, which is an active area of academic and commercial research and development. An exemplary biophotonic integrated circuit can be used to sense absorption spectra (and/or changes in absorption spectra associated with bodily functions (e.g., as in pulse oximetry) or to deliver optical stimulation to particular portions of the body (e.g., as in optogenetics). It could also be used to stimulate and/or sense fluorescent emissions from naturally occurring fluorophores and from fluorescent markers. For instance, the waveguide's surface may be coated, textured, or otherwise treated to attract fluorescent markers that can be stimulated or detected via the evanescent tail extending from the mode(s) guided by the waveguide. In certain cases, visible or infrared light may couple into and out of the waveguide evanescently as well. An additional application includes excitation and collection of inelastic (for example Raman) scattered light.

Conventional CMOS and SOI CMOI Integrated Circuits

FIG. 1A shows the cross-section of a generic bulk CMOS technology die 100 as used in standard electronic circuits. The CMOS technology die 100 is based on a silicon substrate 110, which has been etched and doped to form a series of electronic devices 140. For example, the substrate 110 may be selectively doped with phosphorous or another suitable acceptor dopant to form n$^+$-doped silicon regions 114 and with boron or another suitable dopant to form p$^+$-doped silicon regions 116. As well understood by those of skill in the art, the n$^+$-doped silicon regions 114 and p$^+$-doped silicon regions 116 may be arranged with intrinsic silicon regions 112 to form the electronic devices 140, which may include field-effect transistors, diodes, photodiodes, and other components in the silicon substrate 100.

A layer of oxide 120 or other suitable dielectric material is deposited onto the etched and doped silicon substrate 110 to isolate the electronic devices 140 from each other. The oxide layer 120 prevents current from flowing between adjacent electronic devices 140. Metal 130 is selectively deposited into voids in the oxide layer 120 to provide electrical connections (contacts) for controlling the electronic devices 140. Unfortunately, the close proximity of metal 130 eliminates suitable points for photonic device fabrication, even by post-process means, from the front-end of the CMOS device 100.

FIG. 1B shows a silicon-on-insulator (SOI) die 102 that also includes a silicon substrate 110 and several electronic devices 140. Unlike the standard CMOS die 100 shown in FIG. 1A, however, the SOI die 102 also includes a buried oxide (e.g., SiO$_2$) layer 150 between the silicon transistors 140 and the silicon substrate 110. Although this buried oxide layer 150 can be used as the cladding for a silicon ridge waveguide (not shown), it also makes the SOI die 102 incompatible with the processes used at about 95% of CMOS foundries worldwide.

Fabricating an Integrated Waveguide in a CMOS Process

FIGS. 2A-2E illustrate a process for integrating an optical waveguide into a CMOS integrated circuit using conventional in-foundry processes and minimal post-foundry processing. Advantageously, this process does not require the addition, subtraction, or significant modification of any of the steps used in the in-foundry portion of the CMOS process. As a result, embodiments of this process can be used with the bulk CMOS process available as a multi-project wafer (MPW) service from IBM, Taiwan Semiconductor Manufacturing Co., United Microelectronics Corporation, ON Semiconductor, ST Micro, and other semiconductor foundries. Embodiments can be used for any suitable electronics manufacturing process, including but not limited to dynamic random access memory (DRAM), flash, bipolar, and BiCMOS processes. They can also be used in dedicated wafer processes through either a custom manufacturing line or dedicated foundry service.

FIG. 2A shows the cross section of a bulk CMOS die 200 designed and fabricated to support integrated front-end optical waveguides after in-foundry processing and before post-processing. Like the bulk CMOS die 100 shown in FIG. 1A, it includes electronic devices 240a and 240b (e.g., transistors, diodes, photodiodes, etc.; collectively, electronic devices 140) formed in the front side 213 of a silicon substrate 210 with intrinsic silicon 212 regions, n$^+$-doped silicon regions 214, and p$^+$-doped silicon regions 216 formed by selectively etching and doping the silicon substrate 210. (The silicon substrate 210 also defines an uncoated back side 211.) Metal 230 forms electrical contacts through a dielectric layer 220, or shallow trench oxide layer, that isolates adjacent electronic devices 240 from each other.

The bulk CMOS die 200 also includes a pair of silicon ridges 262a and 262b (collectively, trench regions 262) formed in a diffusion region 260 between the electronic devices 240a and 240b. These ridges 262 define the paths of the optical waveguides to be integrated into the die 200. In general, the ridges' width(s), heights, and general pattern can be laid out for the desired final deposited waveguide optical design using standard tools and techniques. For instance, the ridges 262 can be patterned using 130 nm (or finer) CMOS processes to define waveguides whose widths and aspect ratios mimic the ridges' widths and aspect ratios. The ridges' widths may range from about 100 nm to about 300 nm and the ridges' heights may be about 50 nm to about 1 µm (e.g., about 200 nm to about 400 nm); they may also be even smaller, e.g., for sub-wavelength metamaterial patterns. The ridges 262 may be buffered or isolated from the electronic devices 240 to prevent post-processing in the photonic integration region (the diffusion region 260 and adjacent portions of the dielectric layer 220) from adversely affecting the electronic devices 240.

The silicon ridges 262 extend into an uninterrupted region of the shallow trench oxide layer 220, which is formed within what becomes the evanscent field region of the optical waveguides. The shallow trench oxide layer 220 can be formed using standard CMOS standard techniques, such as including an active silicon fill block layer or excluding other active silicon regions. In some cases, the shallow trench oxide layer 220 may be about 2-3 µm thick; the exact thickness may be determined by the waveguide's desired optical properties. The shallow trench oxide layer 220 may include silicon dioxide, nitrides, or any other suitable oxide with a refractive index lower than that of the waveguide core (e.g., less than 2.2, less than 1.6, etc.).

For CMOS processes including a silicidation step, the silicidation sub-process may optionally be blocked over the active silicon regions (the diffusion ridge 262b that defines the waveguide region) in the CMOS die 200. In addition, little to no metal 230 is deposited on or above or the ridges 262 or the rest of the diffusion region 260 (the future mode field region(s) for the waveguides) to reduce extrinsic propagation loss.

If desired, control elements, such as polysilicon heaters and metal field electrodes, can also be included and positioned relative to the ridges 262, the diffusion region 210, and the electronic devices 140. For instance, FIG. 2A shows a polysilicon strip 250 deposited between the lefthand silicon ridge 262a and a nitride layer 252, which acts as a silicide block. The silicide block can be implemented as something other than a nitride layer in the CMOS process. And if the polysilicon strip 250 is formed for use as a heater, then it can be optionally silicided as well.

The polysilicon strip 250 may affect the transverse profile of the mode(s) guided by the optical waveguide, e.g., via evanescent coupling of the guided mode(s) from the optical waveguide. The polysilicon strip 250 can be used to heat the waveguide core so as to shift the waveguide core's refractive index. (The heater could also be made in the metal layers 230.) Polysilicon heater leads (not shown) can be connected to the polysilicon strip 250 through in-foundry process metallization as shown for the FET devices 140 in FIG. 1A. As readily understood by those of skill in the art, a thermally induced refractive index shift can be used for phase modulation, interferometric intensity modulation, and switching of the guided optical beam(s). The polysilicon strip 250 (or electrodes formed of metal 230 using in-foundry processes) can also be used as field electrodes to apply an electric field to an electro-optically active waveguide core so as to electro-optically shift the waveguide core's refractive index.

Figure 2B:
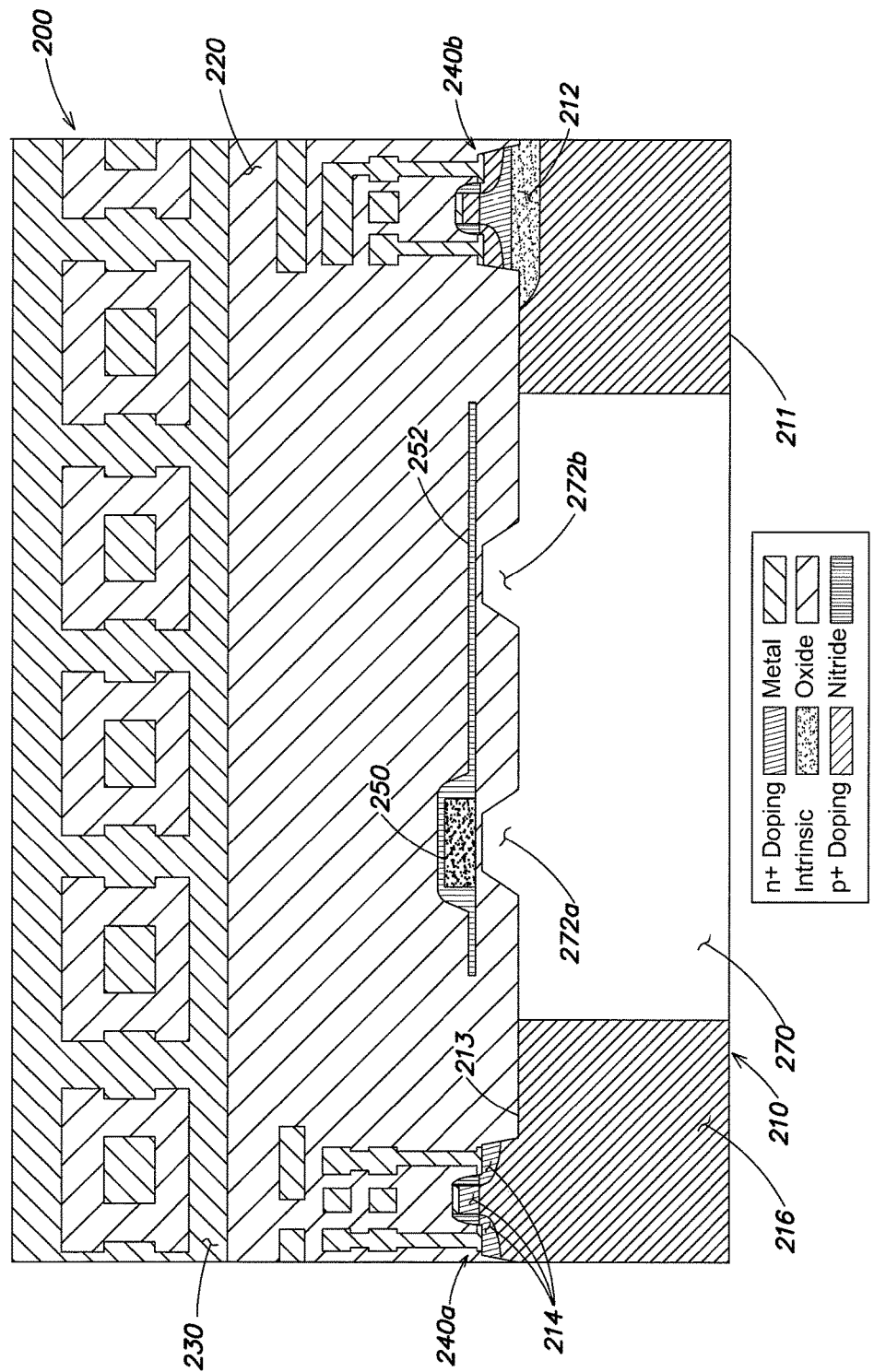
FIG. 2B shows a cross section of the bulk CMOS electronics of FIG. 2A after localized $XeF_2$ release of a portion of the silicon substrate.

FIG. 2B illustrates the bulk CMOS die 200 after the first post-processing step in the fabrication process. In this case, the silicon diffusion region 260 and silicon ridges 262 have been etched away to form a recess 270 in the silicon substrate 210. As explained in greater detail below, after the in-foundry processing is complete, the silicon substrate 210 is etched from the back side 211 to form the recess 270, which extends through the silicon substrate 210 to the front side 213, exposing the surface of a portion of the dielectric layer 220. This etching step also transforms the silicon ridges 262 into trenches 272a and 272b (collectively, trenches 272) whose aspect ratios and dimensions conform to the shapes and dimensions of the silicon ridges 262 as discussed above. In this case, the left-hand trench 272a defines the cross section of a hybrid post-process nitride and in-process polysilicon waveguide. And the right-hand trench 272b defines the cross section of a nitride-only post-process waveguide.

The pattern resolution and front-side alignment accuracy of this step silicon etching may be relatively coarse so as not to present a fabrication burden. And because these trenches 272 define the shapes and sizes of the optical waveguides, there is no need to etch any high-resolution features in post-processing—the waveguides have been defined using high-resolution, in-foundry processes that form the silicon ridges 262.

Figure 2C:
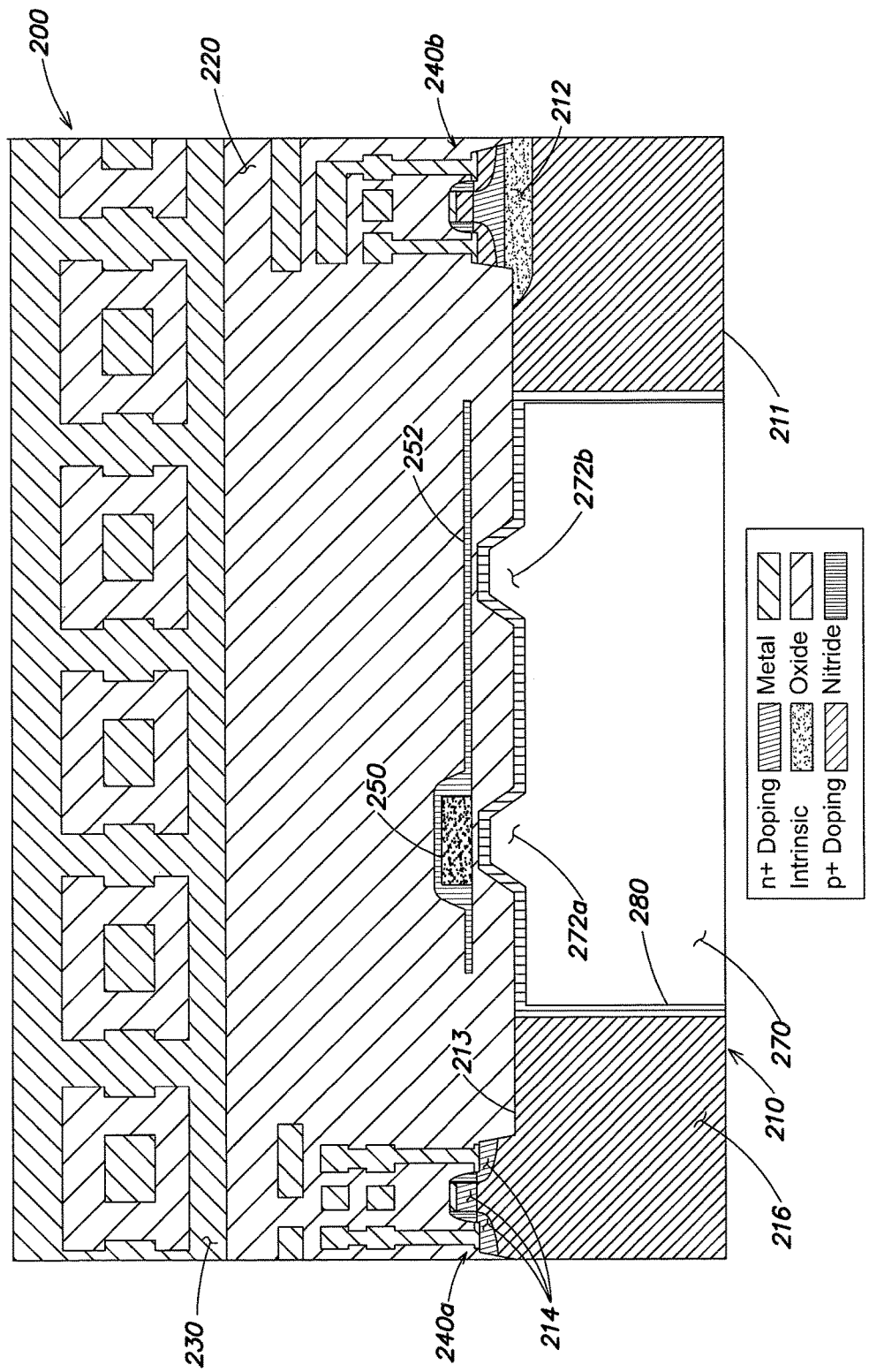
FIG. 2C shows a cross section of the bulk CMOS electronics of FIG. 2B after initial nitride deposition in the recess formed by etching the silicon substrate.
Figure 2D:
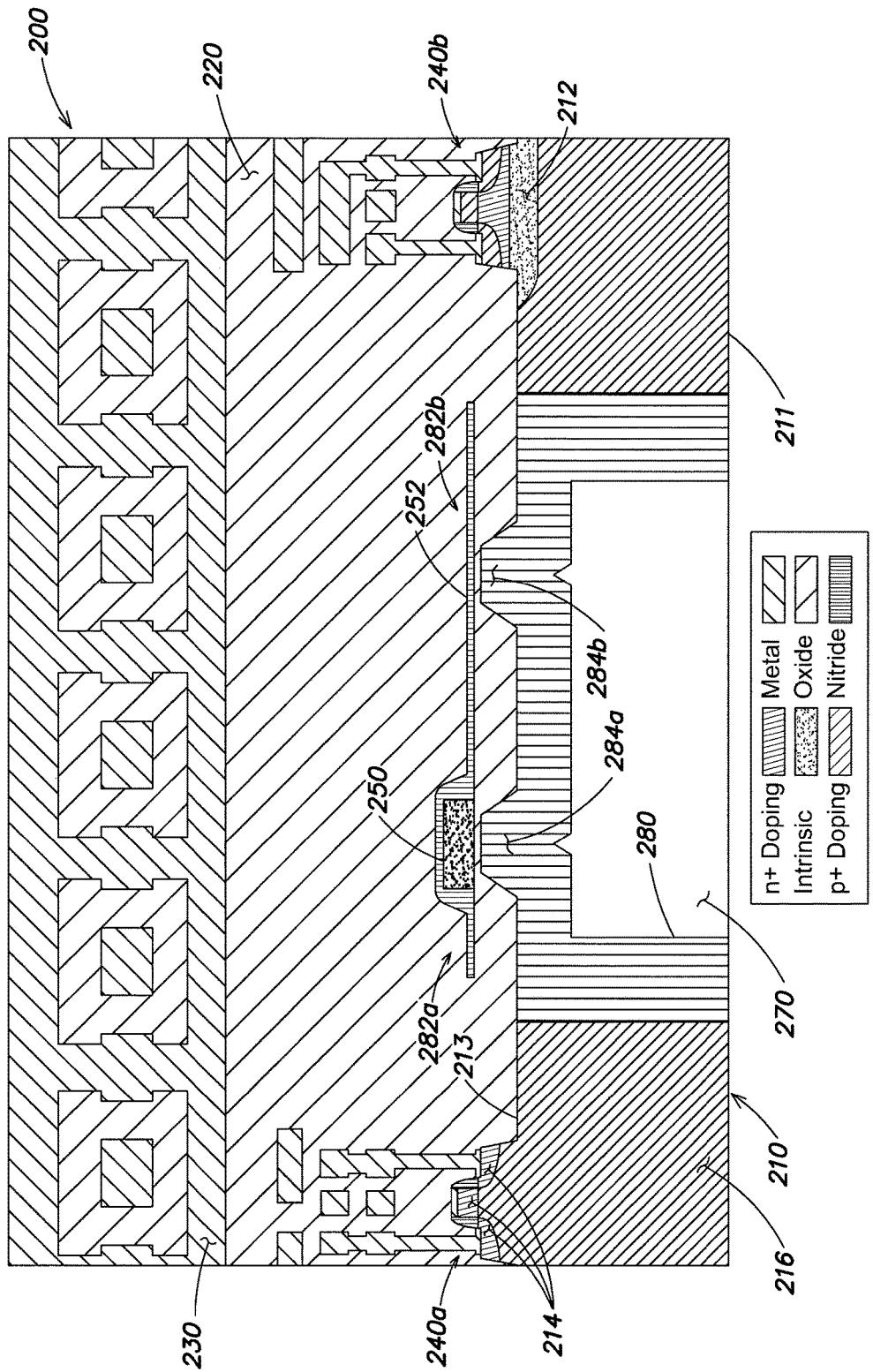
FIG. 2D shows a cross section of the bulk CMOS electronics of FIG. 2C after final nitride deposition in the recess.

Next, a waveguide core material 280, such as a dielectric with a refractive index higher than that of the dielectric layer 220, is deposited within the recess 270, as shown in FIGS. 2C and 2D. This waveguide core material 280 forms a layer of uniform thickness that fills the trenches 272 and covers some or all of the exposed surface(s) of the silicon substrate 210 and the dielectric layer 220 defining the recess's boundaries. (FIG. 2C shows the waveguide core material 280 layer at an intermediate stage of deposition; FIG. 2D shows the layer at its final thickness.) Suitable waveguide core materials 280 include but are not limited to amorphous silicon, silicon nitride, silicon-rich silicon nitride, aluminum oxide, polycrystalline silicon, amorphous silicon germanium, polycrystalline silicon germanium, amorphous silicon carbide, polycrystalline silicon carbide, and silicon oxynitride.

In some cases, a cladding material or other layer may be deposited in the trenches 272 before deposition of the waveguide core material 280, with the waveguide core material 280 deposited on the cladding material. For instance, a low-index cladding may be deposited on a high-index dielectric layer 220 to support a mid-index waveguide core material 280 (i.e., a waveguide core material whose refractive index is lower than that of the dielectric layer 220). Alternatively, or in addition, layers of different waveguide core materials may be deposited sequentially to form a graded-index core (a core whose refractive index profile varies with height) or a prismatic element that refracts or reflects light out of the trench. If the layers are fine enough (e.g., less than a fraction of an optical wavelength), then this layering could be used to form a reflector, transmission filter, or other similar element.

The waveguide core material 280 deposited in the trenches 272a and 272b forms integrated optical waveguides 282a and 282b (collectively, waveguides 282), respectively, each of which has a respective core 284a, 284b (collectively, cores 284). In operation, these waveguides 282 guide light propragating orthogonally to the cross-sectional plane shown in FIG. 2D. As readily understood by those of skill in the art, the exact wavelength range, loss, dispersion, and number of modes guided by each waveguide 282 depends on the waveguide core material 280, the refractive index difference between the waveguide core material 280 and the dielectric layer 220 and the size and shape of the waveguide's cross section. For instance, the waveguide core material 280 may be transparent at visible wavelengths and therefore suitable for guiding visible light. It could also be transparent at infrared wavelengths and therefore suitable for guiding infrared light. Similarly, thicker waveguides or waveguides with larger refractive index contrasts may guide more modes than thinner waveguides or waveguides with smaller refractive index contrasts. The exact thickness and composition of the waveguide core material 280 may be selected based on the desired application.

Figure 2E:
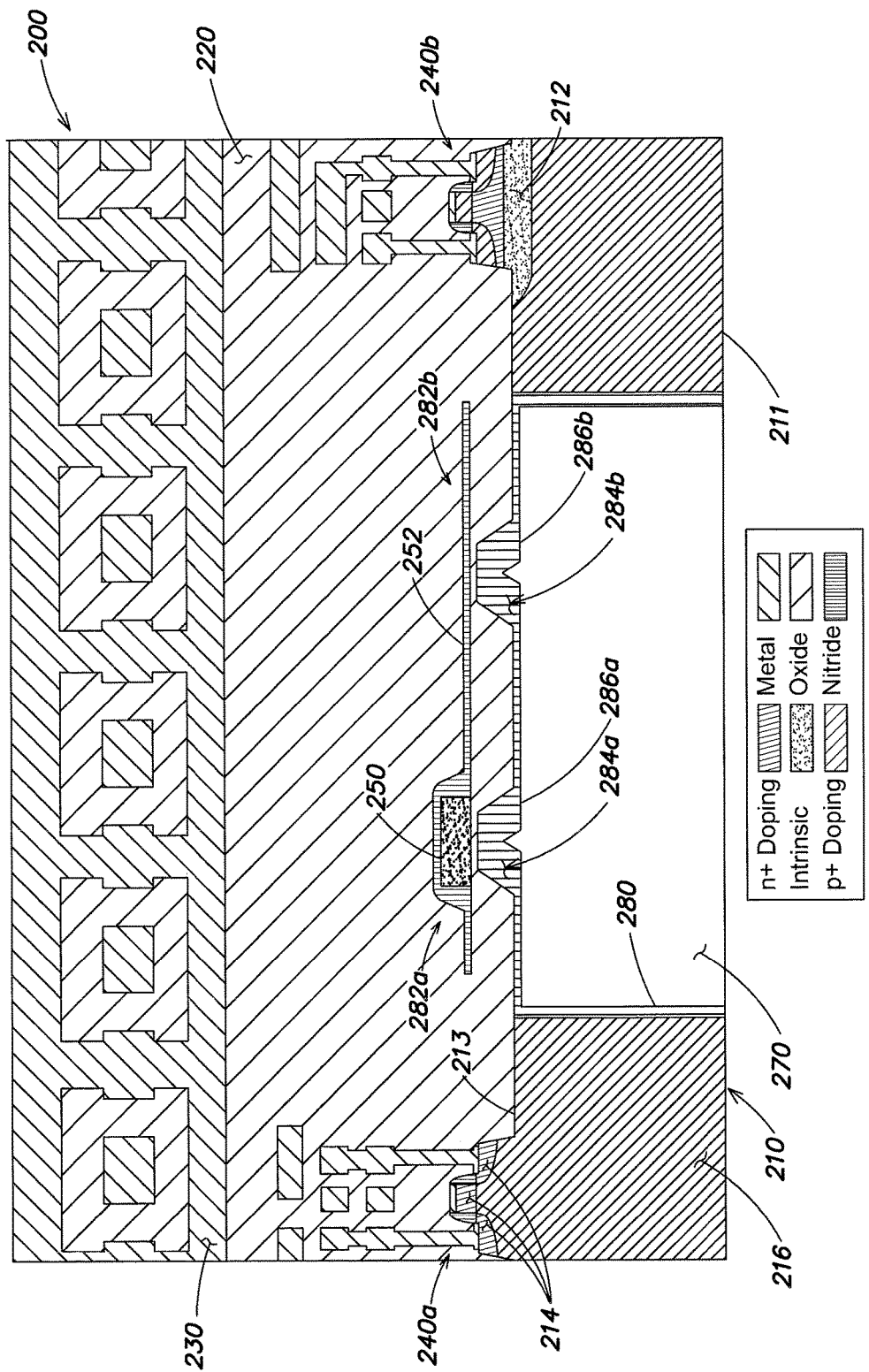
FIG. 2E shows a cross section of the bulk CMOS electronics of FIG. 2D after optional etching of the nitride deposited in the recess.

If desired, excess waveguide core material 280 may be removed from the recess's surfaces, leaving waveguide core material 280 deposited mainly in the trenches 272 as shown in FIG. 2E. For example, the waveguide core material 280 can be etched back without a mask. Removing any excess waveguide core material 280 is an optional step; the waveguides 282 may function with or without waveguide core material 280 extending beyond the trenches 272 and over the exposed portion(s) of the dielectric layer 220. But removing excess waveguide core material 280 changes each waveguide's shape to more closely match the shape of the corresponding trench 272.

Removing excess waveguide core material also exposes surfaces 286a and 286b (collectively, surfaces 286) of the waveguide cores 284a and 284b, respectively. In operation, these exposed surfaces 286 can be used to evanescently couple light into or out of the waveguide cores 284. They can also be used for sensing: for example, a particle on or close to a particular waveguide surface 286 may absorb some or all of the evanescent tail extending from the corresponding waveguide core 284, leading to a change in the spectral intensity distribution of the optical wave propagating through the waveguide core 284. If desired, the exposed surfaces 286 may be coated, textured, or patterned to promote interaction with certain types of molecules for biological and chemical sensing.

Figure 2F:
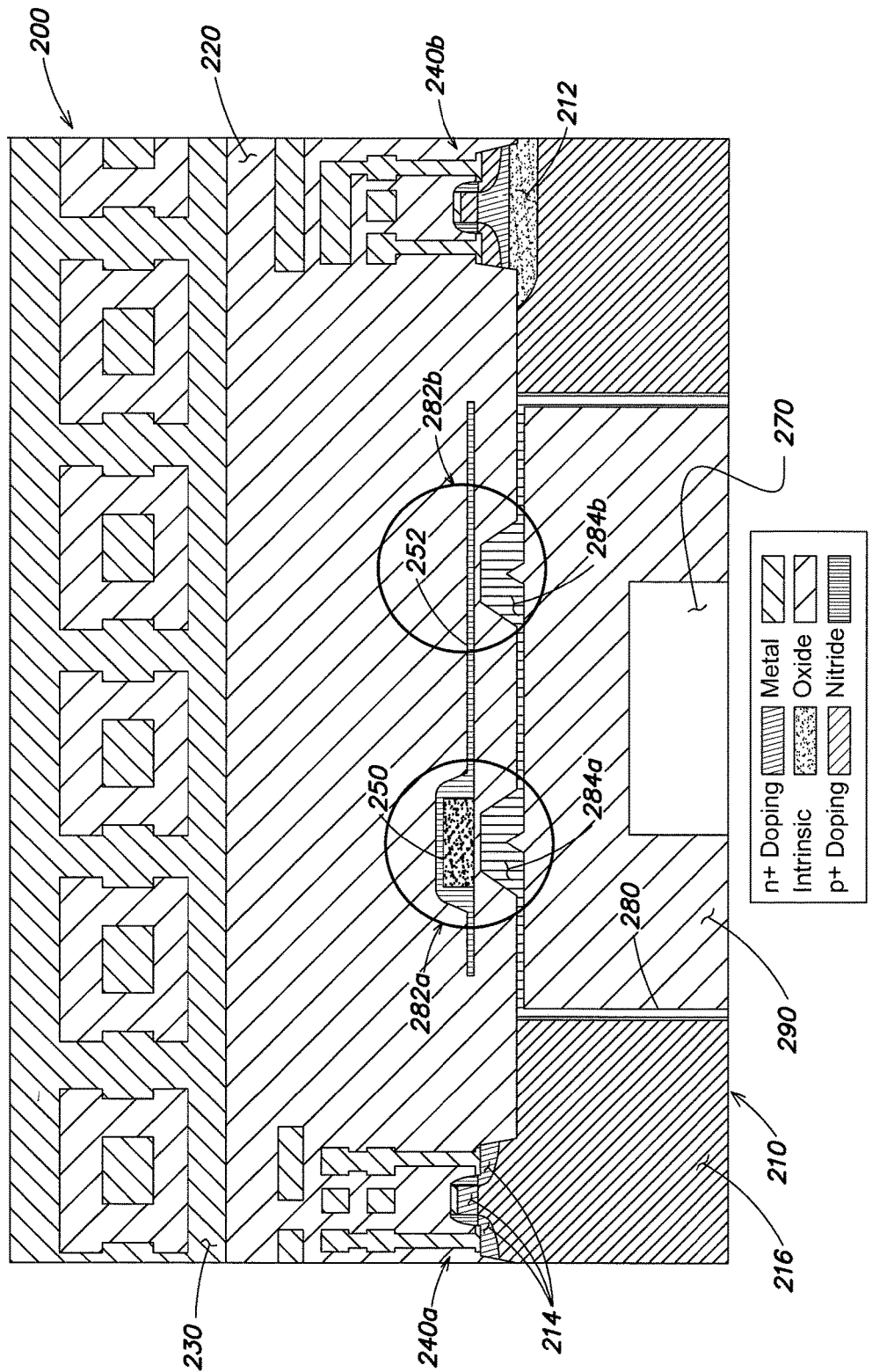
FIG. 2F shows a cross section of the bulk CMOS electronics of FIG. 2E after optional deposition of a lower cladding layer etching of the nitride deposition.

The waveguide cores 284 can also be coated with a cladding layer 290, such as a layer of silicon dioxide or another suitable dielectric as shown in FIG. 2F. (Circles indicate the cross sections of the completed waveguides 284.) The cladding layer 290 has a refractive index that is lower than that of the waveguide core material 280 to confine light within the waveguide cores 284 as readily understood by those of skill in the art. In some cases, the cladding layer 290 covers the exposed surfaces of the waveguide cores 284 as well as adjacent exposed portions of the dielectric layer 220.

In other cases, the waveguide core material 280 is not etched at all, and the cladding layer 290 is deposited directly on the waveguide core material 280. For instance, the cladding layer 290 may serve primarily to protect the waveguide core material 280 rather to confine light within the waveguide cores 284. In other cases, the cladding layer 290 may act as a reactive layer for biophotonic or chemical sensing as discussed above. For instance, the cladding layer 290 could comprise a liquid solution that includes an analyte.

Figure 2G:
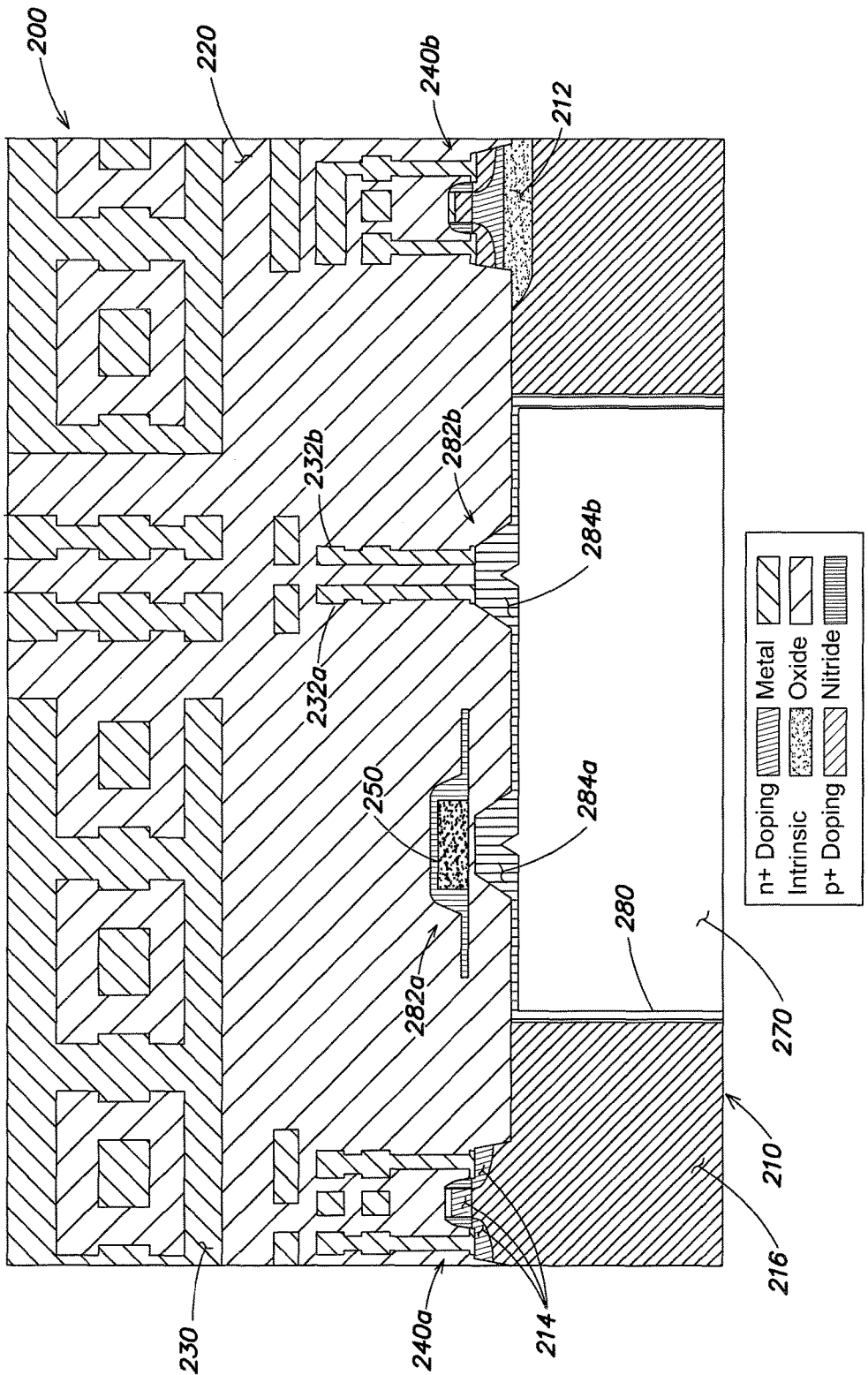
FIGS. 2G and 2H show a cross section of a bulk CMOS device fabricated according to methods illustrated in FIGS. 2A-2F with electrical contacts to apply electrical signals to a waveguide structure in the device.
Figure 2H:
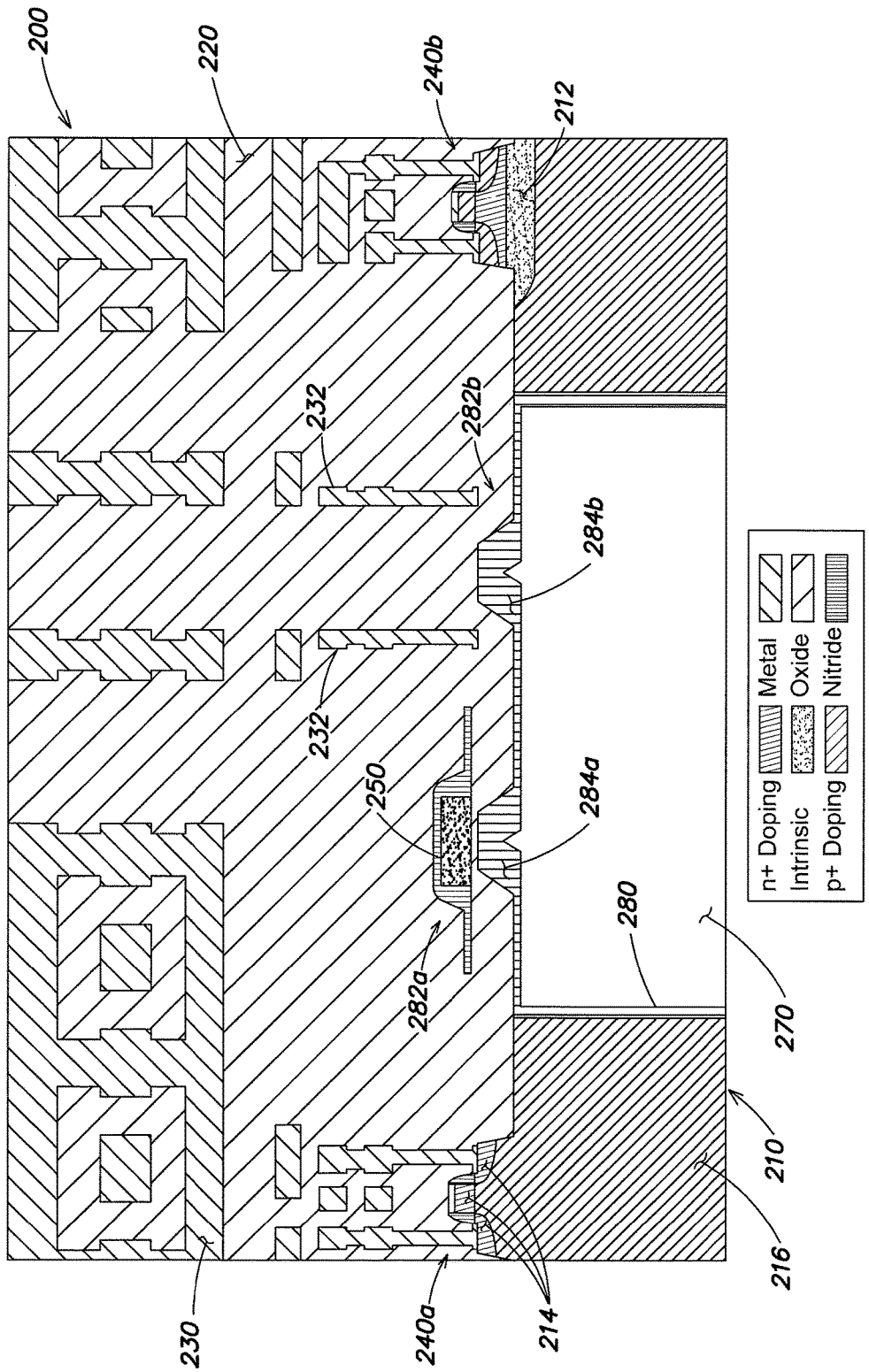
Figure 21:
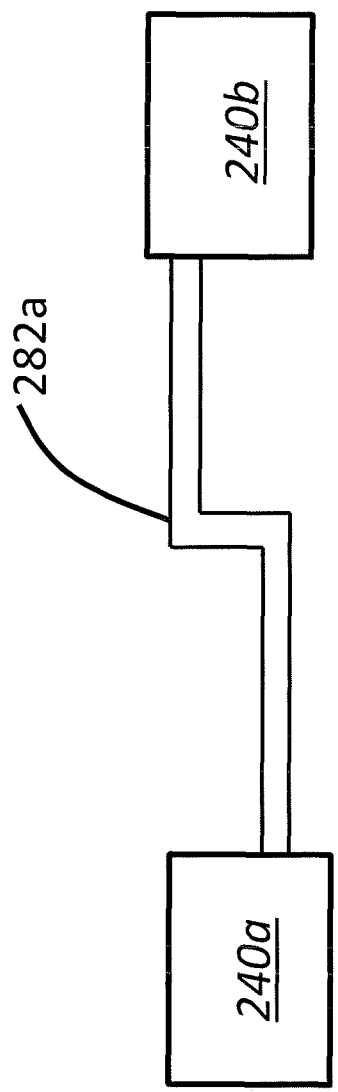

FIGS. 2G and 2H show cross sections of a bulk CMOS device 200 fabricated according to methods illustrated in FIGS. 2A-2F. The device 200 has a pair of electrical contacts 232a and 232b (collectively referred to as electrical contacts 232) to apply electrical signals to the optical waveguide 282b and possibly associated devices such as a grating, a resonator, or a photonic crystals, among others. The metal contacts 232 can be the metal layers used in integrated circuit (IC) processes (e.g., CMOS, Bi-CMOS, etc.), in which metal layers are used to contact integrated electronic components (e.g., transistors or resistors). These metal layers, for example, can be the contacts to the source, drain, and gate in a CMOS process or poly resistors. The electrical contacts 232 can be disposed above the top of the optical waveguide 282b (as shown in FIG. 2G) or away from the optical waveguide 282b (as shown in FIG. 2H) depending on the specific application. For example, in applications where an electrical field is desired, the electrical contacts can be disposed away from the waveguide to reduce optical losses in the contacts 232. The electrical contacts 232 can be either in direct contact with the core material 284b, slightly away from the core material 284b (e.g., in contact with the dielectric layer 220), or both.

FIG. 2I shows a top view of the bulk CMOS device 200 shown in FIG. 2H, illustrating that the optical waveguide 282a defines an optical path between the electronic devices 240a and 240b.

In operation, the electrical contacts 232 can apply several types of electrical signals to adjust the performance of the device 200. In one example, the electrical contacts can apply a voltage and/or an electrical field to the core material 284b, inducing an electro-optic effect, also referred to as Pockel's effect. The electro-optic effect can change the refractive index of the core materials 284b, and accordingly tune the propagation of light in the optical waveguide. In another example, the electrical contacts can apply a voltage and change the charge density in the volume or on the surface of the core material 284b, which can also tune the refractive index and light propagation in the waveguide. In another example, the electrical contacts 232 can drive an electrical current through the optical waveguide 282b, which may have an active core material 284b. The electrical current can pump the active core material 284b to stimulate light emission and induce lasing action. In another example, the electrical contacts 232 can drive an electrical current for Joule heating and induce a thermo-optic effect that can adjust the refractive index in the optical waveguide 282b. In another example, the electrical contacts can include one or more electrical heaters (e.g., via Ohmic heating) to induce the thermo-optic effect by, for example, heating the core material 284b, the dielectric layer 220, or both.

In some cases, one or more pn junction can be defined in the silicon ridge 262. The pn junctions can be fabricated by, for example, a combination of lithography and ion implantation on the back side of the substrate 210. For instance, the pn junctions can be defined in the CMOS process using the well implants available for a boutique of transistors in any technology node. The lithography can define the geometry of the pn junction (e.g., location, shape, dimensions of the junction regions), and the ion implantation can introduce the dopants into the semiconductor materials with desired concentrations.

Selectively Removing Silicon from the Back of a CMOS Substrate

Figure 3A:
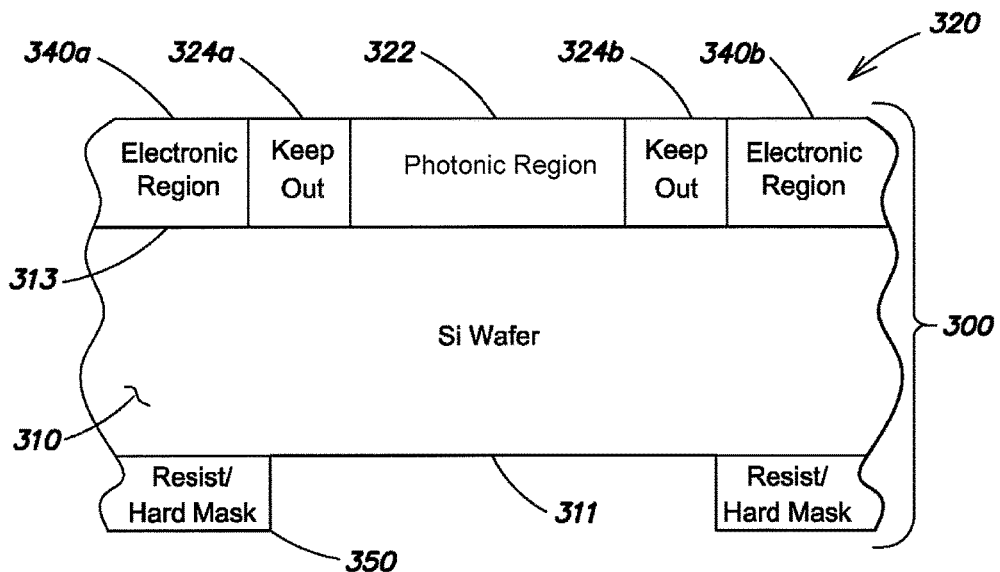
FIGS. 3A-3E illustrate various processes for selectively etching the back of a silicon wafer between electronics regions formed in the silicon wafer to form a recess in the silicon wafer and trenches in a dielectric layer on the silicon wafer.

FIGS. 3A-3E illustrate different processes for selectively etching the back of a CMOS platform to form a recess, e.g., as shown in FIG. 2B. FIG. 3A shows the cross section of a CMOS die 300 after in-foundry processing. Like the CMOS platform 200 shown in FIGS. 2A-2F, the CMOS die 300 in FIG. 3A includes a silicon substrate 310 that defines a front side 313 coated with a dielectric layer 320 and an uncoated back side 311 opposite the front side 313. The dielectric layer 320 is subdivided into a photonics region 322, which will define trenches for integrated optical waveguides once etching is complete, bordered by a pair of exclusion or "keep-out" regions 324a and 324b (collectively, exclusion regions 324). Each exclusion region 324a, 324b isolates the photonics region 322 from a corresponding electronics region 340a, 340b (collectively, electronics regions 340), which may contain one or more transistors, photodiodes, or other electronic devices or components.

Optionally, the back side 311 of the silicon substrate 310 may be etched, polished, or lapped before being etched to form the recess and trenches. For example, the back side 311 may be etched to remove furnace depositions resulting from in-foundry deposition steps. In addition, some silicon substrates—including many of those used for electronics manufacturing—are not polished on both sides. If the back side 311 has a rough surface, the surface roughness may complicate the patterning and other process steps required for waveguide formation. Polishing also removes any unwanted dielectric layers from the silicon substrate's back side 311 as well. Lapping the back side 311 removes unwanted dielectric layers, reduces surface roughness, and thins the silicon substrate 310 itself, which in turn reduces the amount of etching required to expose the shallow trench isolation layer (dielectric layer 320) through the back side 311.

FIG. 3A also shows a resist or hard mask 350 that covers certain portions of the silicon substrate's back side 313. This mask 350 defines a coarse pattern for the optical waveguides being formed in the CMOS die 300 and protects the electronics regions 340 from the processing performed for waveguide integration. The mask 350 and patterning are not required if the design is purely photonic and there aren't any transistors to be protected. The mask 350 and patterning can also be omitted if etch selectivity is utilized in the following processing, such as by employing electrochemical etches to stop on specific doping layers or metallurgical junctions. Otherwise, standard photolithography can be used to pattern the back side 311 of the silicon substrate 310.

As readily understood by those of skill in the art, the back-side pattern can be aligned to features (e.g., transistors) on the front side 313 of the silicon substrate 310 using a back-side aligner (not shown) or other fiducial mark. Suitable options for aligning the back-side pattern to the front-side features include placing alignment features on the wafer's back side 311 using a front-to-back aligner or by directly aligning to the front-side features using a back-side aligner. Regardless of any alignment process, the resulting photoresist pattern 350 masks the electronics regions 340 and exposes the photonics region 322 for further processing as shown in FIG. 3A.

In some cases, the fabricated electronics, including any exposed metal pads (e.g., on the front side of the CMOS wafer 300), may be protected with a photoresist or other layer during post-processing. This photoresist may be removed after post-processing to expose the metal pads for packaging, etc.

Once any desired masks (e.g., mask 350) are in place, the silicon substrate 310 is selectively etched to define a recess that from the back side 311 to the front side 313 of the silicon substrate 310. (Any dielectric layers on the back side 311 may be removed using a non-selective etch.) There are many suitable etch strategies, including selective vapor phase etching, selective wet etching, selective dry etching (e.g., deep reactive ion etching (DRIE)), multi-step etching, and mechanical polishing combined with selective etching.

Figure 3B:
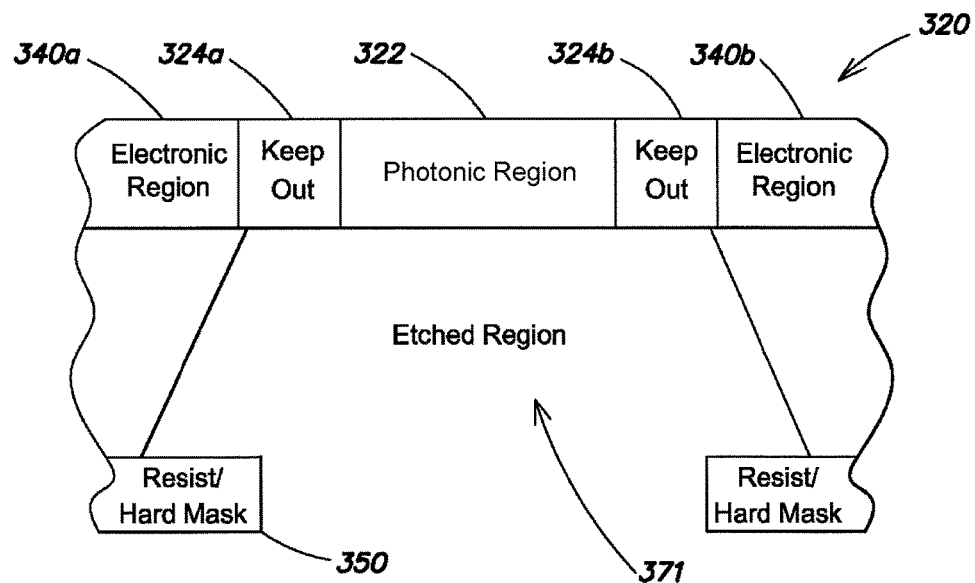

FIG. 3B shows a recess 371 formed in the die 300 of FIG. 3A using selective vapor phase etching. An extremely high etch rate selectivity is achievable using the vapor phase etchant $XeF_2$. Starting from the exposed back side 311, the $XeF_2$ etches through the entire thickness of the silicon substrate 310 and stops at the front-end dielectric layer 320, with minimal etch damage to any in-foundry designed shallow trench isolation features formed in the dielectric layer 320. One benefit of an $XeF_2$-like etch's extremely high selectivity is that the the high-threshold voltage gate oxide may protect the polycrystalline silicon transistor-gate layer used in the transistors in the electronics regions 340, even for oxide layers with thicknesses below 10 nm. Similarly, the dielectric layer 320 may protect polycrystalline silicon used as an alternate photonic device layer. However, the etching's isotropic nature may cause poor front-side to back-side registration and result in larger "keep-out" regions 324 between the electronics regions 340 and the photonics region(s) 320.

Figure 3C:
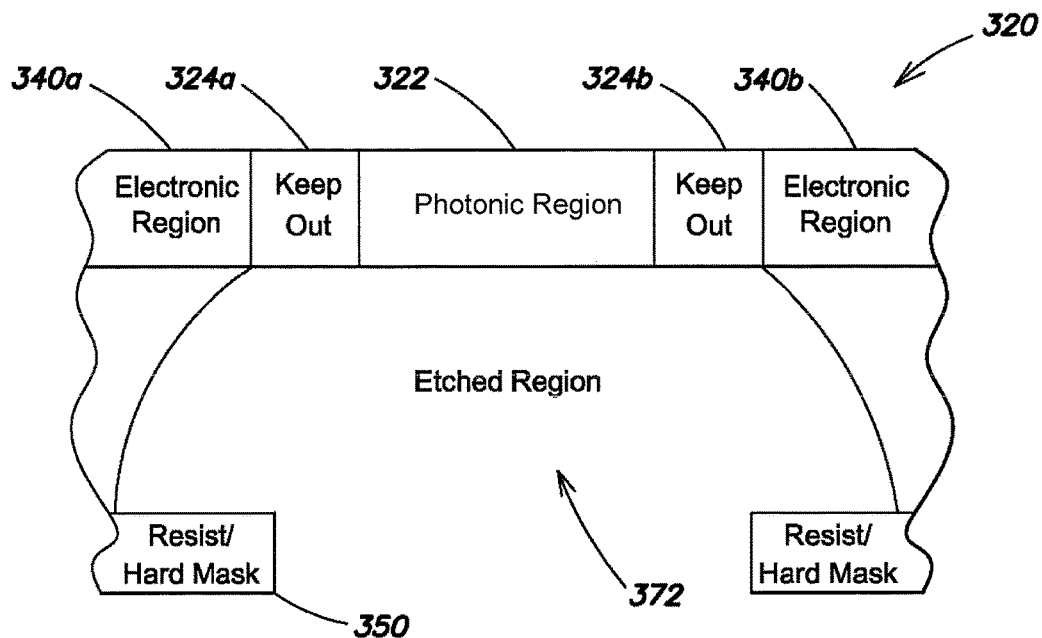

FIG. 3C shows a recess 372 formed in the die 300 of FIG. 3A using selective wet etching. As understood by those of skill in the art, an NaOH-based wet etch stops on the buried oxide layer of a SOI wafer after etching through the full thickness of the silicon handle. Similarly, NaOH-based wet etching can be used to expose trenches and other patterns in the dielectric layer 220 with a minimum of pattern degradation. Although anistropic etching is possible, common etch angles may be near 50 degrees, which is comparable to an isotropic etch.

Figure 3D:
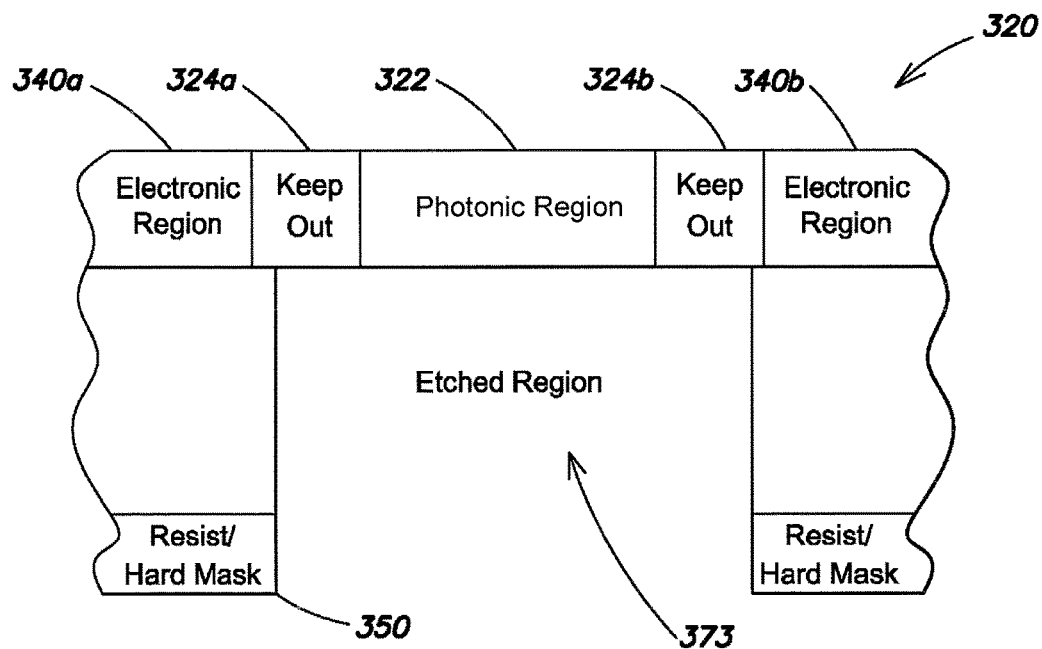

FIG. 3D shows a recess 373 formed in the die 300 of FIG. 3A using selective dry etching. For instance, deep reactive ion etching (DRIE) enables modest selectivity between silicon and silicon dioxide (e.g., a selectivity of approximately 10:1). In certain cases, DRIE yields a recess 373 with a relatively high aspect ratio, e.g., as shown in FIG. 3D. But because DRIE may exhibit lower selectivity than selective vaper phase etching or selective wet etching, care should be taken to prevent selective dry etching from degrading the trenches for waveguide formation in the dielectric layer 320.

Figure 3E:
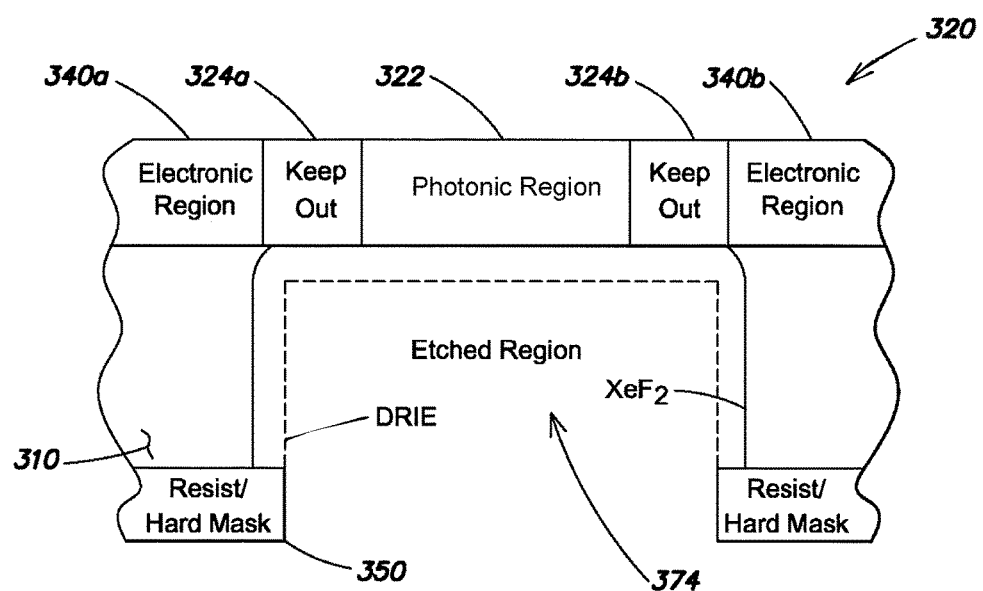

FIG. 3E shows a recess 374 formed in the die 300 of FIG. 3A using multi-step etching. Since DRIE and chemical (e.g., wet or vapor-phase) etching approaches offer different advantages, they can be combined in a multi-step etch. In some cases, multi-step etching can result in high etch aspect ratios for improved front-side to back-side registration and a small separation between the electronic and photonic regions. In the case shown in FIG. 3E, DRIE is used to etch away most of the silicon substrate 310 to yield a high aspect ratio. The remaining portion of the silicon substrate 310 is removed with a high selectivity chemical etch to reduce possible front-side pattern degradation that might otherwise because caused by using less selective DRIE. And because the chemical etch is relatively brief, it is less likely to cause alignment degradation due to its relatively low etch aspect ratio.

Depositing Dielectric Materials to Form Waveguides

As explained above, etching the back side of the silicon substrate exposes the front-side patterns (trenches) formed during in-foundry processing for waveguide definition while leaving the wafer's electronic regions protected by the original silicon substrate. Once the patterns have been exposed, they can be filled or covered with the dielectric materials that form the waveguide core and optional lower cladding as illustrated in FIGS. 4A-4H. As readily understood by those of skill in the art, the core dielectric layer can be chosen to achieve desired performance (e.g., a given desired index contrast, transmission wavelength range, dispersion characteristics, etc.).

Figure 4A:
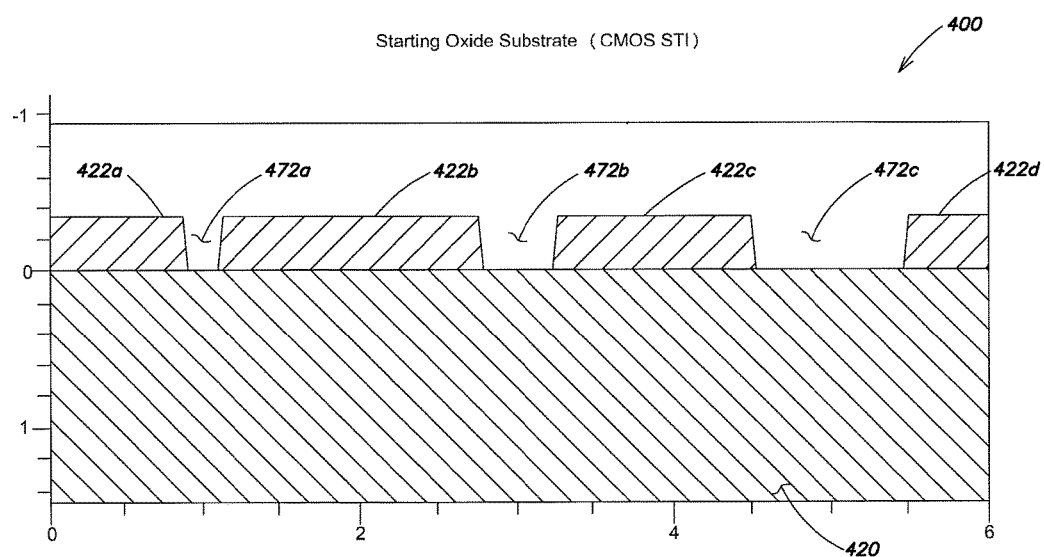
FIG. 4A shows a cross section of a starting oxide substrate for CMOS shallow trench isolation (STI).

FIG. 4A shows the cross section of a patterned template region 400 suitable for integrated waveguide formation process simulations. (The views in FIGS. 4A-4H are rotated 180 degrees from the views of FIGS. 1-3.) The back side of the silicon substrate (not shown) has been etched to form expose the front-side patterns (trenches) 472a, 472b, and 472c (collectively, trenches 472) formed during in-foundry processing for waveguide definition while leaving the wafer's electronic regions protected by the original silicon substrate. The trenches are 300 nm deep and have widths from left to right of 0.25 µm (trench 484a), 0.50 µm (trench 484b), and 1.00 µm (trench 484c). The trenches are defined by respective shallow-trench isolation features 422a-422d (collectively, features 422) in the post-waveguide lower cladding oxide, which may form part of a CMOS backend dielectric stackup 420.

Figure 4B:
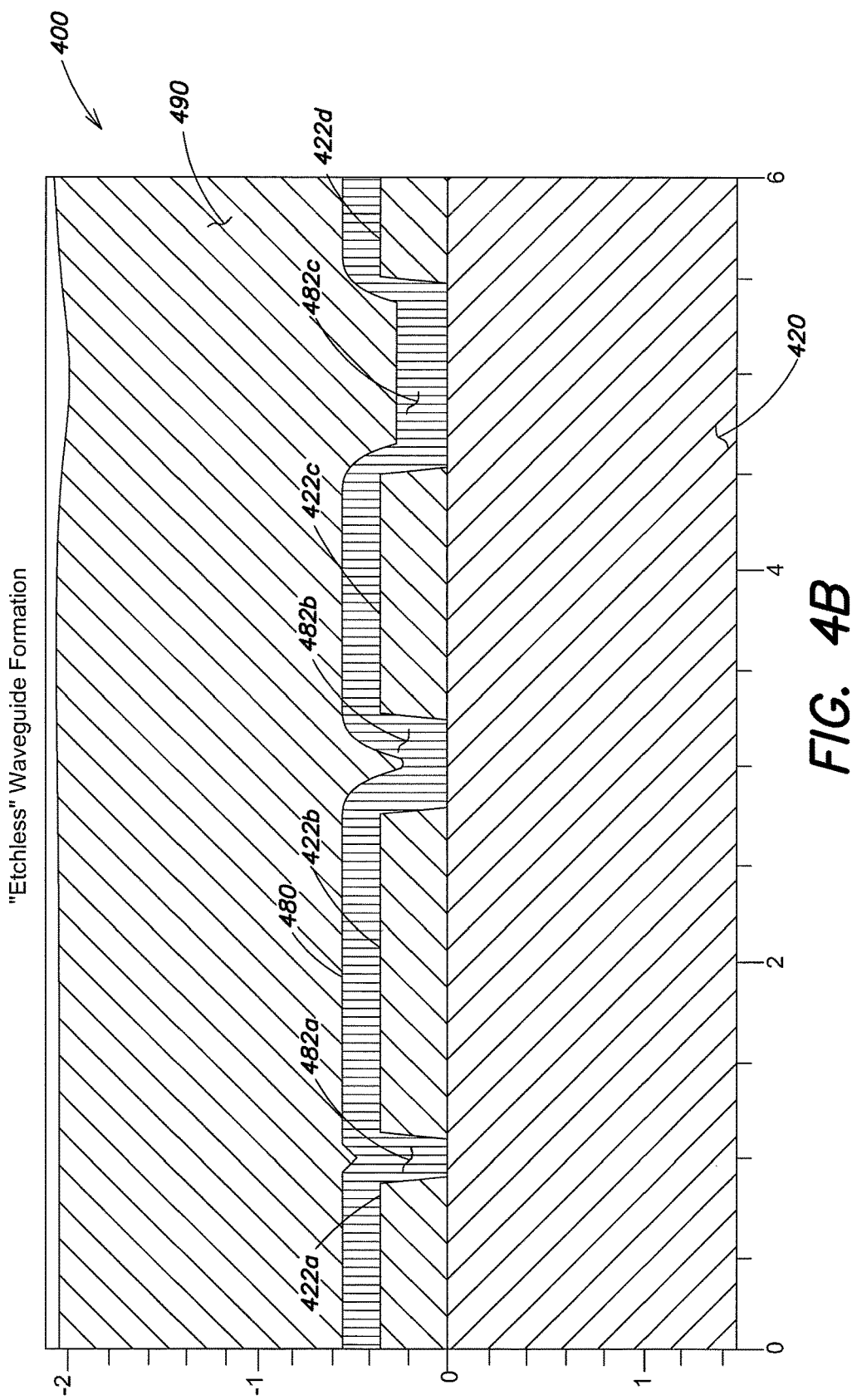
FIG. 4B shows a cross section of "etchless" waveguides formed in the oxide substrate shown in FIG. 4A.

FIG. 4B shows the CMOS die 400 after deposition of a uniform layer of waveguide core material 480 on the exposed portions of the dielectric layers 420 and the shallow-trench isolation features 422. In this case, the deposited waveguide core material 480, which may include amorphous silicon, silicon nitride, silicon-rich silicon nitride, or aluminum oxide, forms core and cladding layers on the in-process front-side patterns with no further processing. The waveguide modes are supported by the local concentration increase of the high-index core layer formed by the isotropic deposition on the patterned sidewall. If desired, an additional dielectric layer 490 (with a refractive index lower than that of the waveguide core material 480) can be deposited over the waveguide core material 480 as a cladding.

More specifically, the waveguide core material 480 deposited in the left-hand trench 472a (FIG. 4A), which has a width that is less than twice the thickness of the deposited waveguide core material 480, forms a waveguide 482a similar to the rib waveguides formed on SOI substrates. The waveguide core material 480 deposited in the central trench 472b (FIG. 4A), which has a width that is greater than twice the thickness of the deposited waveguide core material 480 and less than the sum of twice the deposited layer thickness and the wavelength of the guided mode(s), forms a waveguide 482b that behaves like a radio-frequency slot waveguide. But the right-hand trench 472c (FIG. 4A) is wider than the sum of twice the deposited layer thickness and the wavelength of the guided mode(s) and therefore may not be able to confine an optical wave.

Figure 4C:
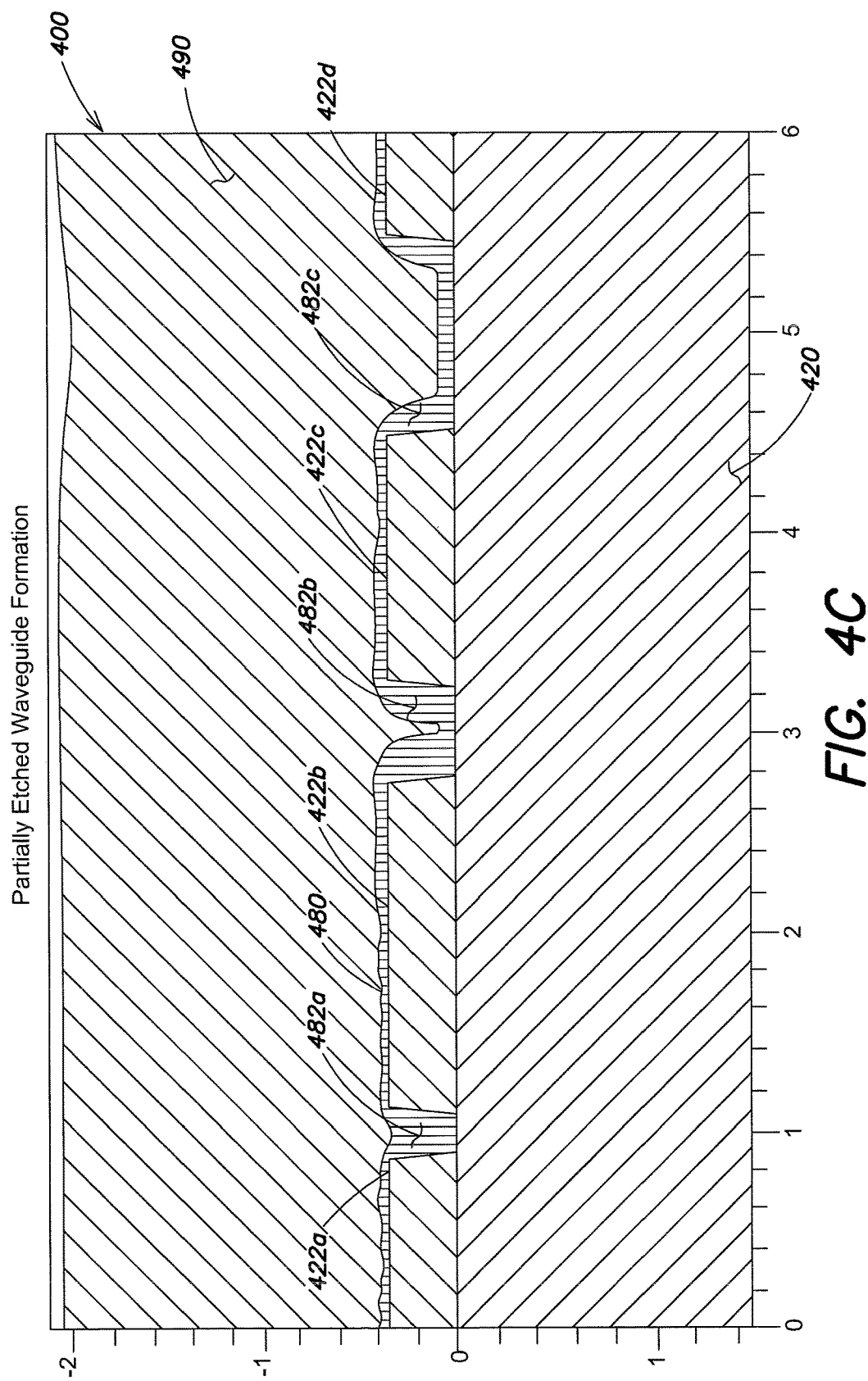
FIG. 4C shows a cross section of partially etched waveguides formed by etching the waveguide layer shown in FIG. 4B.
Figure 4D:
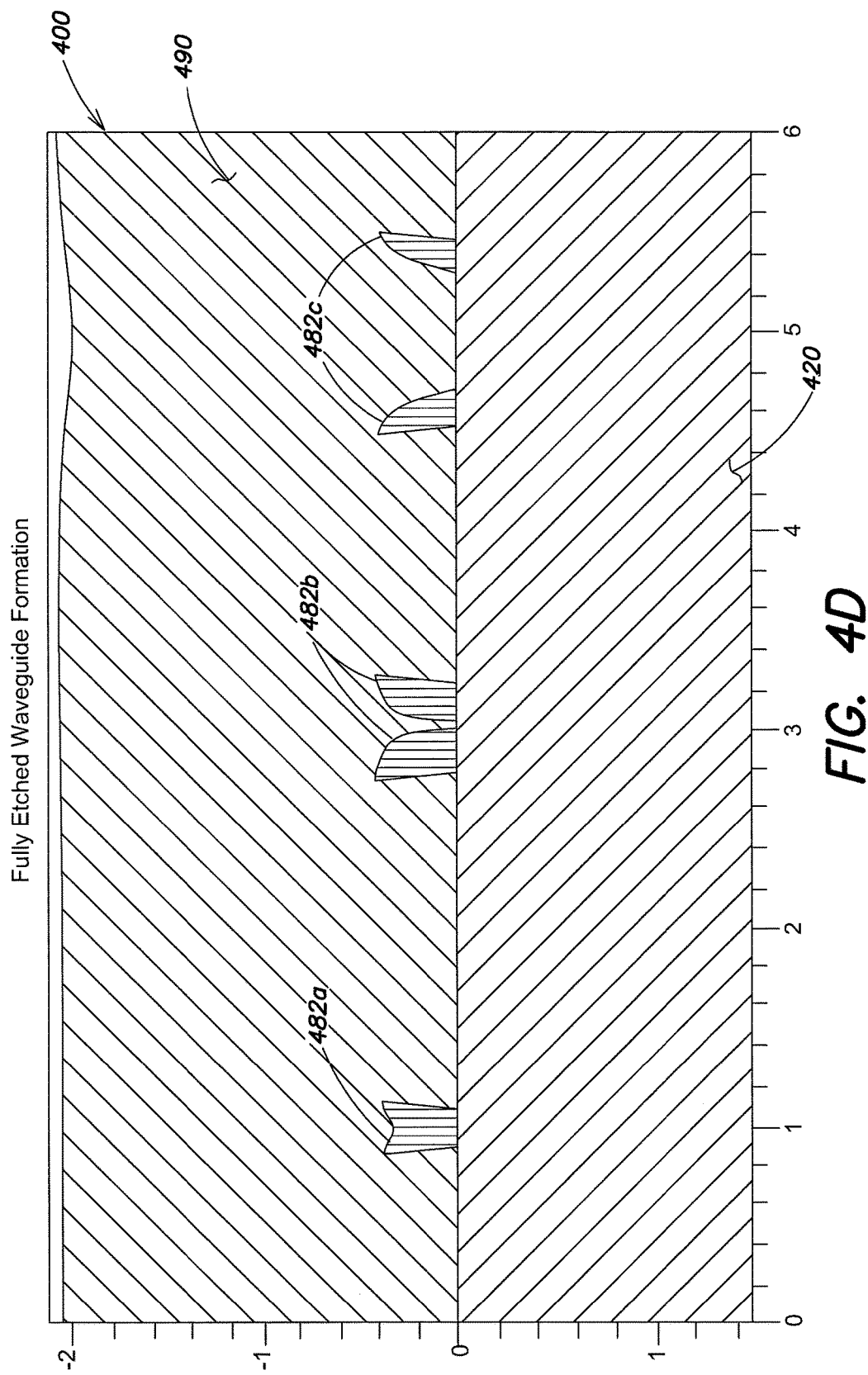
FIG. 4D shows the cross section of fully etched waveguides formed by etching the waveguide layer shown in FIGS. 4B and 4C.

If desired, the waveguide core material 480 can be anisotropically etched prior to the deposition of the lower-cladding dielectric layer 490 as shown in FIGS. 4C and 4D. For example, FIG. 4C shows that partial etching may leave the core of the left-hand waveguide 482a intact, but not the central waveguide 482b or the right-hand waveguide 482c. Full etching, as shown in FIG. 4D, leaves intact only the core of the left-hand waveguide 482a and splits the other waveguides 482b and 482c into separate pieces, each of which may guide one or more distinct optical modes. In certain cases, full etching may be used to create separate waveguide cores that are too close together to be defined by separate trenches or narrower than the resolution limit of the in-foundry CMOS process. In addition, etching the waveguide core material 480 may roughen the dielectric layer surface and result in higher integrated mode loss. Nevertheless, removing excess waveguide core material increases the left-hand waveguide's effective lateral index contrast, which can increase lateral confinement.

Figure 4F:
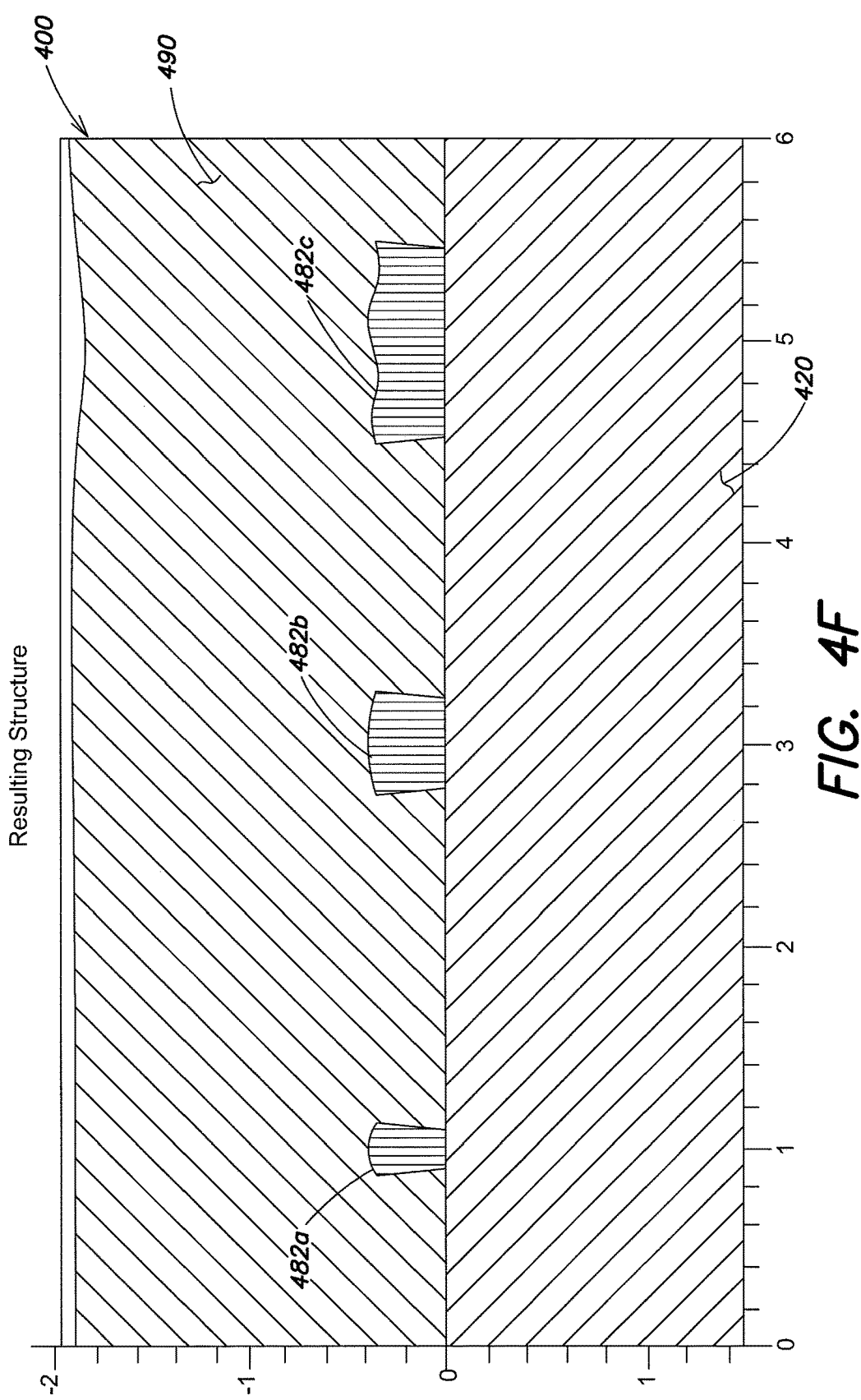
FIG. 4F shows a cross section of a waveguide structure fabricated using the overgrowth for quasi-planarization shown in FIG. 4E.

FIGS. 4E and 4F illustrate formation of integrated optical waveguides on the CMOS wafer 400 of FIG. 4A through deposition, planarization, and etching of waveguide core material 480. Planarization yields a surface that is suitable for further processing and that does not necessarily reflect the topology of the front-end waveguide pattern. One way to produce a planar surface is to over-deposit the waveguide core layer and then polish, lap, or etch the waveguide core layer to the desired thickness. As shown in FIG. 4E, isotropic deposition of a relatively thick (e.g., 1.5 µm thick) layer of waveguide core material 480 mitigates the effects of the front-end topology (e.g., the STI features) on the waveguide core material's upper surface—the thicker layer has a smoother upper surface than a thinner layer. Etching away the extra waveguide core material 480 and depositing a cladding layer 490 yields the waveguides 482 shown in FIG. 4F. Depositing the thicker layer of waveguide core material 480 results in a right-hand waveguide core 482c that may behave like a slab waveguide.

Figure 4G:
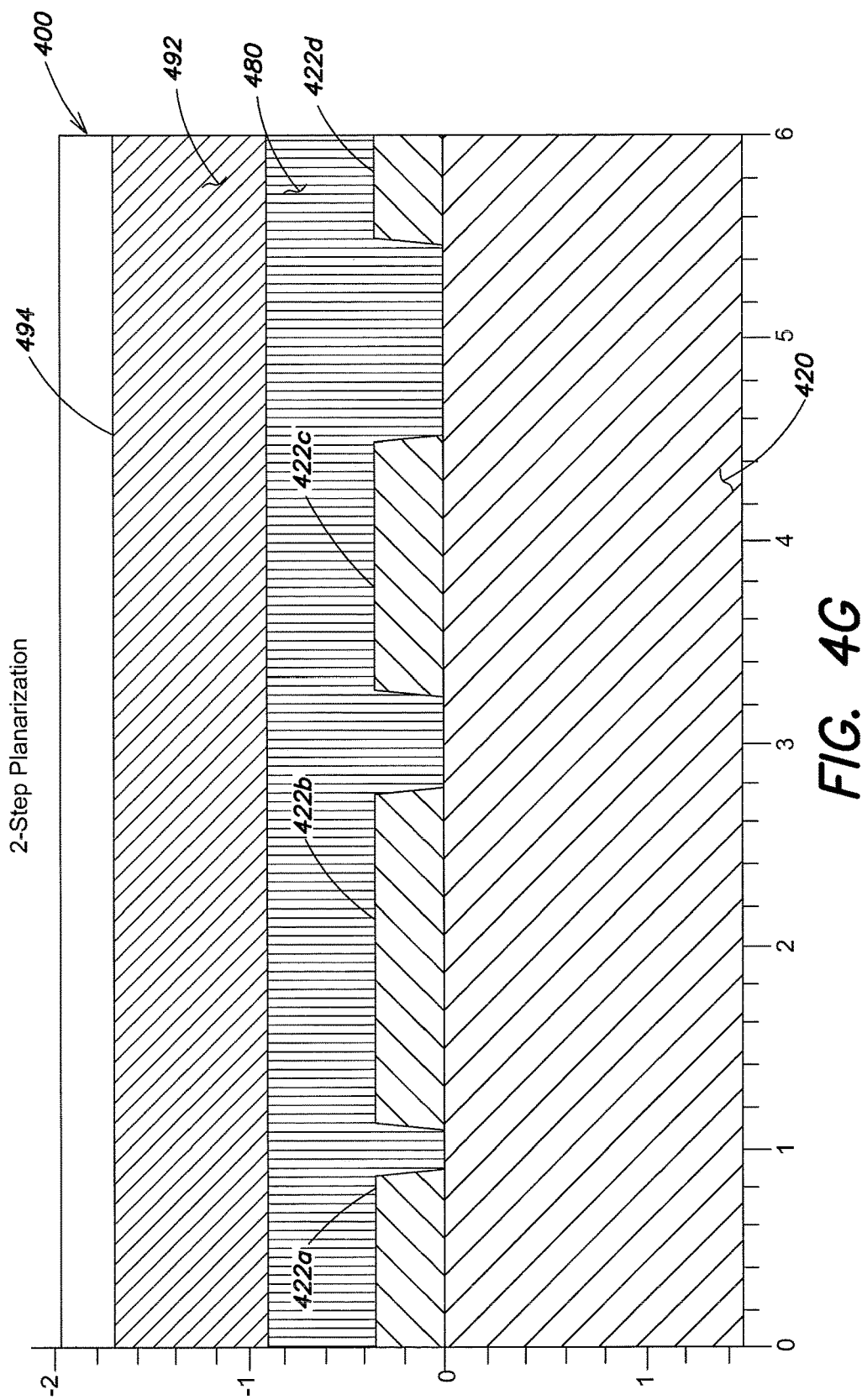
FIG. 4G shows a cross section of a waveguide structure undergoing a two-step planarization using a sacrificial layer and a waveguide core layer.
Figure 4H:
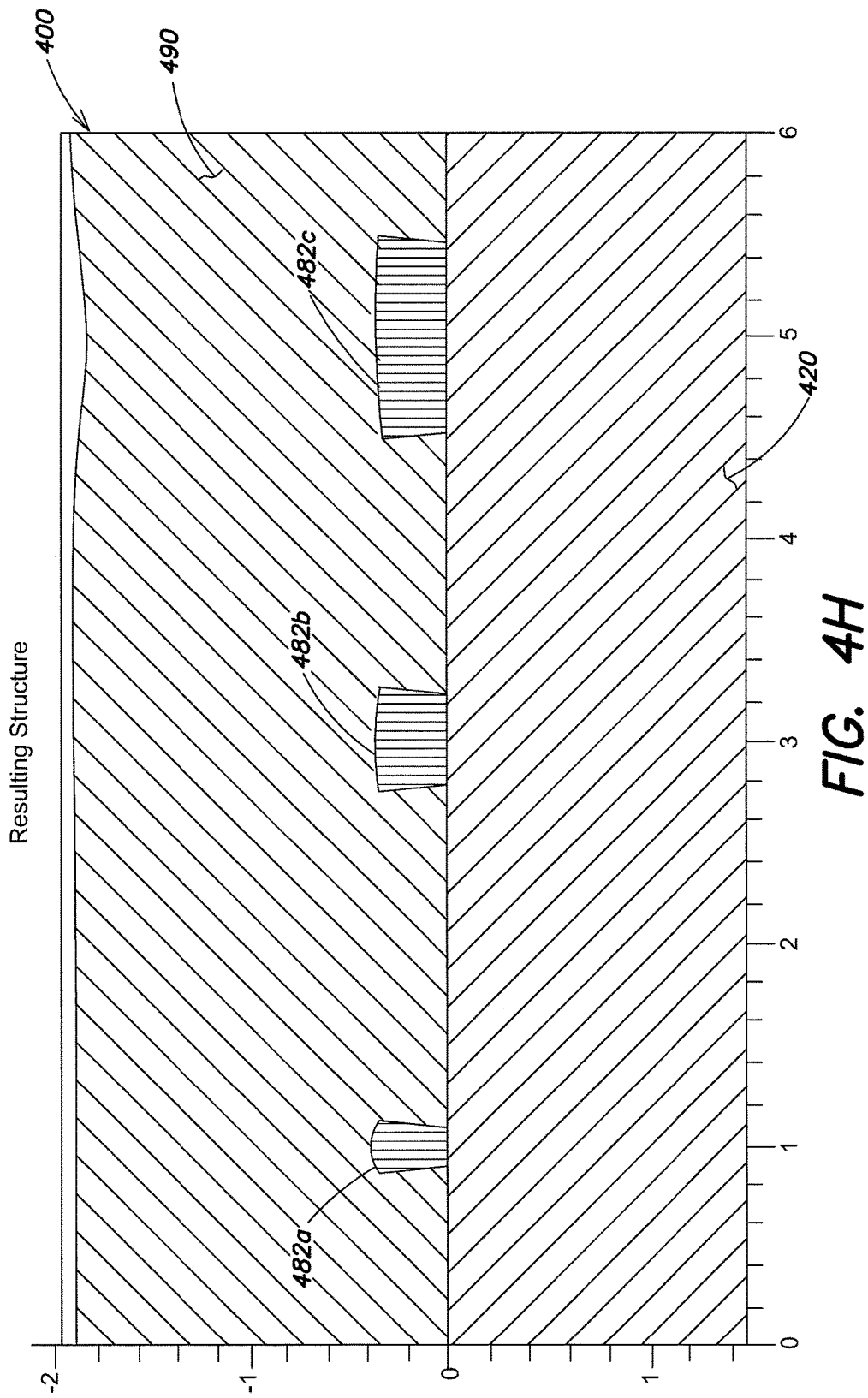
FIG. 4H shows a cross section of a waveguide structure fabricated using the two-step planarization shown in FIG. 4G.

FIGS. 4G and 4H illustrate waveguide deposition and planarization on the CMOS wafer 400 of FIG. 4A using a sacrificial layer 492 to perform planarization prior to waveguide core etch-back. In this case, the waveguide core material 480 is deposited as a layer that is thicker than the final waveguide cross-section, but not necessarily thick enough to be planarized itself (e.g., about 400-500 nm thick). Next, a relatively thick sacrificial layer 492 (e.g., about 1 µm thick) of material that can be etched at a rate similar to the etch rate of the waveguide core material 480 is deposited and planarized to form a top surface 494 whose shape and roughness are independent of the front-end pattern topology. Planarization of the sacrificial layer can be accomplished by any suitable technique, including but not limited to spin coating, reflow, repeated deposition and etch, and embossing. The planarized sacrificial layer 492 and waveguide material 480 are then etched back to form uniform thickness waveguide cores 484 for any pattern width as shown in FIG. 4H.

Simulated Waveguide Performance

Figure 5A:
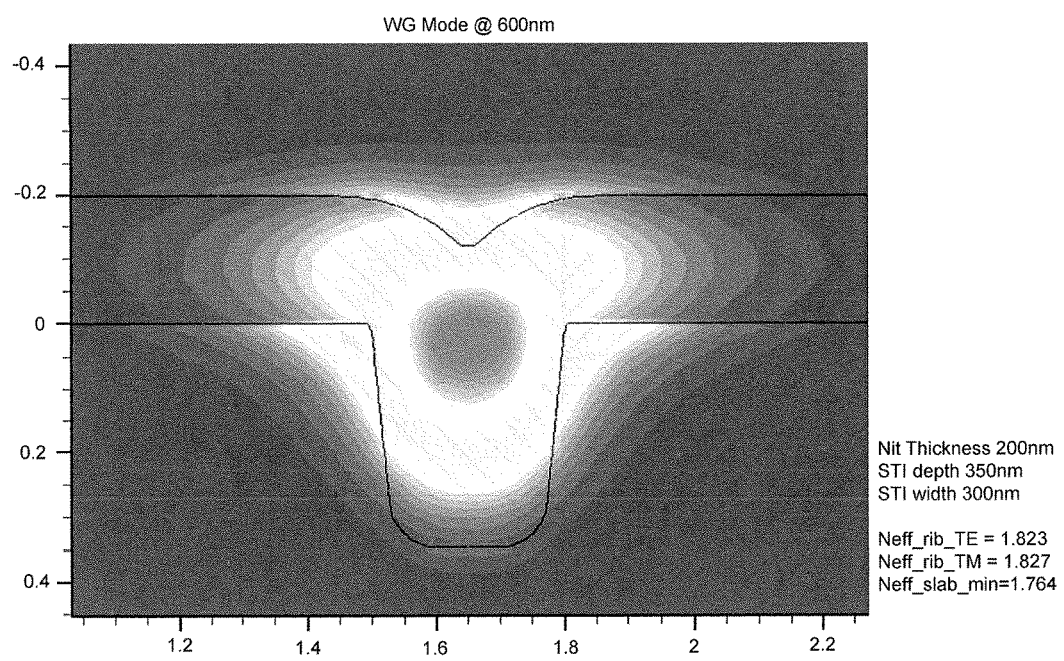
FIG. 5A is a plot of the simulated profile of a waveguide mode at a wavelength of 600 nm in an exemplary integrated optical waveguide.
Figure 5B:
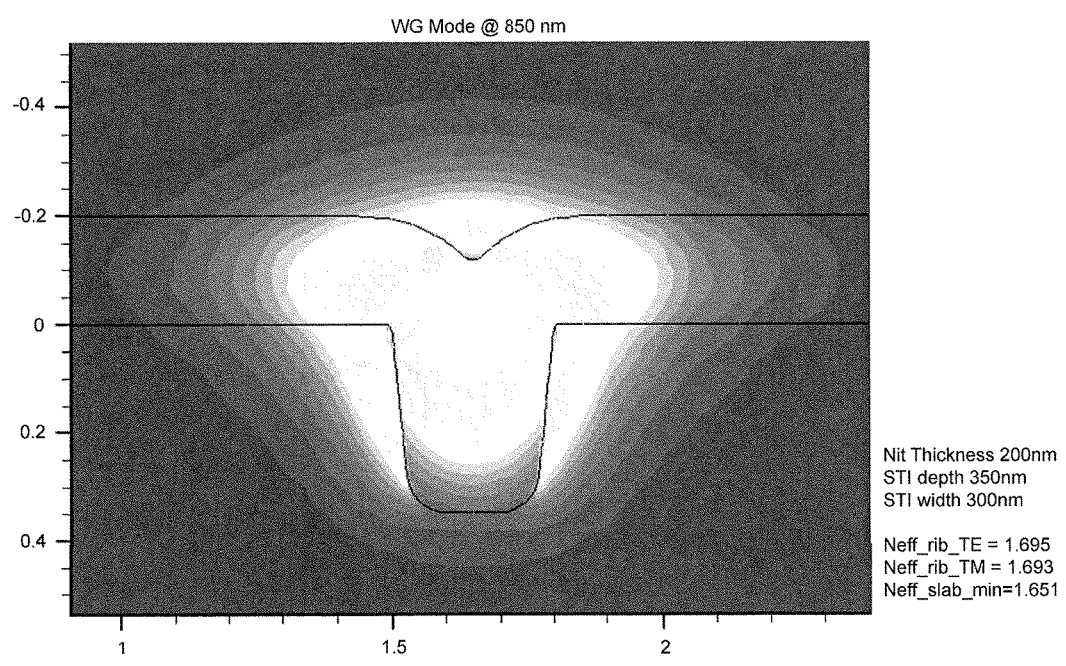
FIG. 5B is a plot of the simulated profile of a waveguide mode at a wavelength of 850 nm in the exemplary integrated optical waveguide of FIG. 5A.

FIGS. 5A and 5B show simulated transverse electric (TE) and transverse magnetic (TM) field optical mode profiles for operating wavelengths of 600 nm and 850 nm, respectively, for a waveguide with a stoichiometric silicon nitride core. The stoichiometric silicon nitride core has a refractive index of approximately 2.0 and is deposited in a trench whose width is about 300 nm and whose depth is about 350 nm. The simulated trench can be formed in a 350 nm shallow trench isolation (STI) layer using commercially available 90 nm bulk CMOS technology. (In the simulation shown in FIGS. 5A and 5B, the silicon nitride also forms a relatively uniform layer with a thickness of about 200 nm that extends over the STI layer. If desired, this layer of silicon nitride can be removed and replaced with a layer of silicon dioxide.)

In operation, the CMOS-based structure shown in FIGS. 5A and 5B supports both TE and TM "rib" waveguide modes that propagate via the silicon nitride in the trench and TE and TM "slab" waveguide modes that propagate via the relatively uniform layer of silicon nitride that extends over the STI layer. Strictly speaking, the rib waveguide modes may be considered as quasi-TE/quasi-TM modes since the rib waveguide has a trapezoidal cross-section. Conversely, the slab waveguide modes may (in principle) be TE/TM modes. As a result, the quasi-TE rib waveguide mode may couple to the TE slab waveguide mode and possibly the TM slab waveguide mode as well.

For instance, at a wavelength of about 600 nm, the effective indices for the simulated quasi-TE and quasi-TM rib waveguide modes are 1.823 and 1.827, whereas the minimum effective index for the slab waveguide modes is about 1.746. At wavelength of 850 nm, these effective indices are about 1.695, 1.693, and 1.651, respectively.

The effective index of the TE slab waveguide mode is higher than the effective index of the TM slab waveguide mode, so the effective index contrast for the quasi-TM rib mode is larger; as a result, the quasi-TM rib waveguide mode may be less susceptible to loss caused by bending or roughness. A full consideration of intermodal coupling between the modes of the rib and those of the slabs for different sources of coupling may provide more information about differences in propagation loss.

Waveguide and Grating Devices Fabricated via CMOS Techniques

Waveguides and gratings fabricated via CMOS techniques described above can find applications in a wide range of areas, including communications and biosensors. For instance, a vertical-coupling grating can be used to couple light from an optical fiber into or out of a CMOS waveguide whose optical axis is parallel to a silicon substrate. One- and two-dimensional periodic structures (e.g., gratings or photonic crystals) can also be used to diffract light within a planeparallel the silicon substrate, possibly for wavelength-division multiplexing, for routing optical signals throughout a chip, etc. The periodicities and materials of these structures may be selected based on the desired operating wavelengths, power coupling ratios, diffraction angles, etc.

Figure 6A:
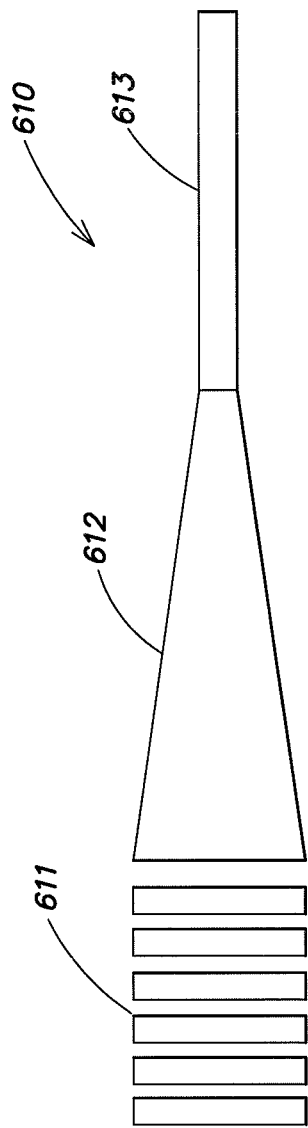
FIG. 6A shows a grating coupler that can be used to couple light into and out of a chip including a waveguide fabricated using methods illustrated in FIG. 2A-2G.

FIG. 6A shows a vertical-coupling component 610 that can couple light into and/or out of a CMOS device or a system (not shown). The component 610 includes a grating structure 611, a tapered region 612, and a small-core waveguide 613, all which can be fabricated using the CMOS techniques disclosed herein. The grating structure 611 can receive light from an out-of-plane fiber (not shown) and couple the light into the tapered region 612, which further couples the light to the waveguide 613. The waveguide 613 may be coupled to a laser or other source, detector, or other waveguide or coupler deposited on the CMOS structure. The tapered region 612 can terminate in a spherical end and achieve a better numerical aperture than a cleaved and polished fiber end, improving coupling efficiency into the small-core waveguide 613.

Figure 6B:
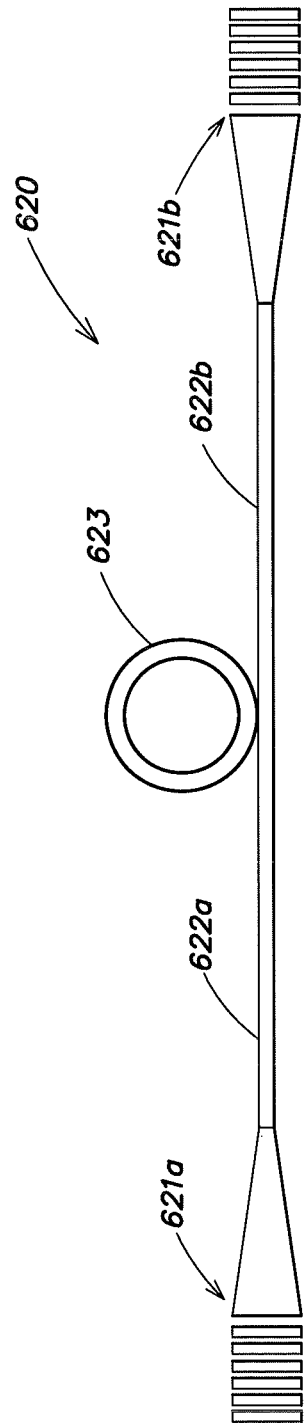
FIG. 6B shows a semiconductor device including a ring resonator and a waveguide fabricated using methods illustrated in FIG. 2A-2G.

The component 610 can be used in a resonator-based sensor 620 as shown in FIG. 6B. The sensor 620 includes a pair of grating coupler 621a and 621b (collectively referred to as 621), a pair of waveguides 622a and 622b (collectively referred to as waveguides 622), and a ring resonator 623, all which can be fabricated using the CMOS techniques disclosed herein. One example of the ring resonator can be a glass microsphere (e.g., with a 100 microns diameter) that can be integrated into the CMOS device and confines light by total internal reflection. In another example, the resonator can be placed on top of the waveguide structure.

In operation, the ring resonator 623 is immersed in or exposed to a sample that is to be analyzed. For example, a drop of the sample may be placed over the ring resonator 623. Light from a tunable laser or other source is coupled into the sensor 620 via the first grating structure 621a and propagates along the waveguide 622b towards the ring resonator 623. At least some of the light is evanescently coupled into the ring resonator 623 and resonates within the ring resonator 623 if an integer number of wavelengths fit on the closed circular optical path. The non-resonant light propagates along the second waveguide 622b towards the second grating structure 621b, which couples the transmitted light to an out-of-plane detector (not shown).

The resonance wavelength appears as a sharp Lorentzian-shaped spectral response in the sensor's transmission spectrum, which can be acquired with a tunable laser source (not shown) coupled to the ring resonator 623 via the optical waveguides 622. The sensor's transmission spectrum can be recorded by sweeping the laser wavelength: as the wavelength of the laser source matches the resonance wavelength of the microsphere, light couples from the optical waveguide to the resonator and a drop of intensity is recorded. The resonance wavelength may change depending on changes in the resonator's optical path length, which can occur, for example, upon binding of biomolecules to the micro-resonator surface. When a biomolecule such as bovine serum albumin protein (BSA) attaches to the equator of the resonator 623, the protein can be polarized within the evanescent field effectively pulling part of the field distribution to the outside of the resonator 623 and thereby slightly increasing the overall optical path length. The binding event can thus be detected from the resulting red-shift of the resonance wavelength.

FIG. 6C shows a directional coupler 603 utilizing the waveguides fabricated according to methods described herein. The directional coupler 630 includes a plurality of ports 631a-631d (collectively referred to as ports 631) to couple light into and out of the pair of waveguides 632a and 632b (collectively referred to as waveguides 632). In operation, light propagating in the first waveguide 632a evanescently couples into the second waveguide 632b (and vice versa). As understood in the art, the amount of power transferred between the waveguides 632 depends on the optical path length of the coupling region, the distance between the waveguides 632, and the wavelength(s) of the propagating beam(s).

The directional coupler 630 can be used to construct an interferometer-based sensor 640 shown in FIG. 6D. The sensor 640 includes a plurality of grating couplers 641a-641d (collectively referred to as grating couplers 641), a pair of directional couplers 642a and 642b (collectively referred to as directional couplers 642), a reference arm 643, and a sensing arm 644. In operation, interaction between a sample and an optical signal propagating in a sensor can produce a change of optical mode effective index and accordingly shift the phase of the optical signal. To convert this phase shift into an amplitude change, interferometer architectures can be employed.

One exemplary interferometer can be a Mach-Zehnder interferometer as shown in FIG. 6D. In this approach, an input optical signal is coupled into the first directional coupler 642a via the first grating coupler 641a or the second grating coupler 641b. The first directional coupler 642a couples a first portion of the input optical signal into the reference arm 643 and a second portion of the input optical signal into the sensing arm 644. The component propagating in the sensing arm 644 interacts evanescently with the sample, producing a sample-dependent phase shift. After the propagation through these two arms, the first and second portions of the input optical signal are combined in the second directional coupler 642b to produce outputs at the second pair of grating couplers 641c and 641d whose intensities depend on the sample-dependent phase shift.

Figure 6E:
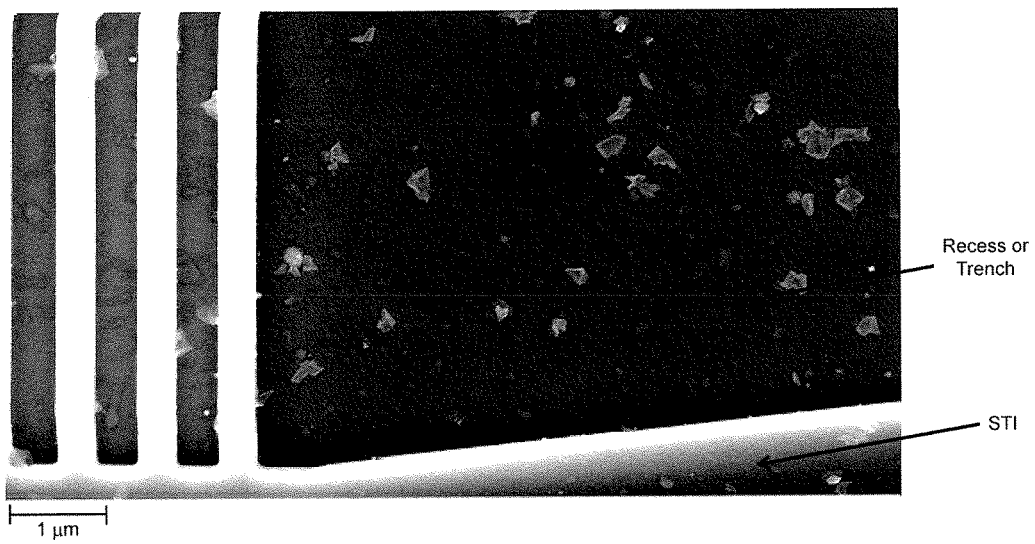
FIG. 6E shows a scanning electron micrograph (SEM) image of a sample grating device, like those shown in FIGS. 6A, 6B, and 6D, fabricated according the method shown in FIGS. 2A-2G.

FIG. 6E shows a scanning electron micrograph of the trench for a sample grating device. The etched trench has a smooth surface with a RMS surface roughness of about 2.21 nm. The depth of the trench is on the order of 200 nm to 400 nm. The grating device after etching can be cleaned using either wet process or dry process to remove possible debris. For example, a wet cleaning can be carried out in de-ionzied water or solvents (e.g., acetone, methanol, or isopropanol), in which an ultrasonic wave can be applied to facilitate the cleaning. In another example, a dry cleaning process can use liquid polymers that solidify after being applied to surfaces of the sample device. Debris on the surfaces can adhere to the liquid polymers during solidification of the liquid polymers and can be removed when the solidified liquid polymers are peeled off from the device.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments (e.g., of designing and/or operating transparent displays) may be implemented using hardware, software, or a combination thereof. When implemented in software, the software code can be executed on any suitable processor or collection of processors, whether provided in a single computer or distributed among multiple computers.

Further, it should be appreciated that the present displays and methods of making and operating displays may be used in conjunction with a computer, which may be embodied in any of a number of forms, such as a rack-mounted computer, a desktop computer, a laptop computer, or a tablet computer. For instance, the controller 140 shown in FIG. 1A may be implemented as a computer, smart phone, or other processor-based device. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices, including one or more displays as disclosed herein. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A semiconductor device comprising:
   a silicon substrate having a front side, a back side, and a first refractive index, and defining a recess extending through the silicon substrate from the back side of the silicon substrate to the front side of the silicon substrate;
   a dielectric layer of first dielectric material, having a second refractive index lower than the first refractive index, disposed on the front side of the silicon substrate, the dielectric layer defining a trench open to the recess defined by the silicon substrate;
   silicon disposed within the trench to form a core of an optical waveguide; and
   a pn junction formed in the silicon disposed within the trench.

2. A semiconductor device comprising:
   a silicon substrate having a front side, a back side, and a first refractive index, and defining a recess extending through the silicon substrate from the back side of the silicon substrate to the front side of the silicon substrate;
   a dielectric layer of first dielectric material, having a second refractive index lower than the first refractive index, disposed on the front side of the silicon substrate, the dielectric layer defining a trench open to the recess defined by the silicon substrate; and
   silicon disposed within the trench to form a core of an optical waveguide,
   wherein the trench has a width of about 250 nm or less.

3. The semiconductor device of claim 2, further comprising:
   a heater, formed in the dielectric layer, to heat the core of the optical waveguide.

4. The semiconductor device of claim 2, further comprising:
   a polysilicon strip, formed in the dielectric layer, to shift a refractive index of the core of the optical waveguide.

5. The semiconductor device of claim 2, further comprising:
   a heater, in thermal communication with the core of the optical waveguide, to thermally induce a shift in a refractive index of the core of the optical waveguide.

6. The semiconductor device of claim 2, further comprising:
- electrodes, in electrical communication with the core of the optical waveguide, to electro-optically induce a shift in a refractive index of the core of the optical waveguide.

7. The semiconductor device of claim 2, wherein the core of the optical waveguide has an exposed surface to evanescently couple light into or out of the core of the optical waveguide.

8. The semiconductor device of claim 7, wherein the exposed surface is at least one of coated, textured, or patterned to promote interaction with certain types of molecules for biological and chemical sensing.

9. The semiconductor device of claim 2, further comprising:
- a cladding layer, disposed directly on the core of the optical waveguide and the dielectric layer, to guide light in the core of the optical waveguide.

10. The semiconductor device of claim 2, wherein the trench extends partway into the dielectric layer.

11. The semiconductor device of claim 2, wherein the core of the optical waveguide has three sides in direct contact with the dielectric layer.

12. The semiconductor device of claim 2, wherein the core of the optical waveguide is configured to guide visible light.

13. The semiconductor device of claim 2, wherein the core of the optical waveguide is configured to guide infrared light.

14. The semiconductor device of claim 2, wherein the core of the optical waveguide has a width of about 50 nm to about 1 μm.

15. The semiconductor device of claim 2, further comprising:
- at least one electronic device formed on the front side of the silicon substrate.

16. The semiconductor device of claim 2, wherein the trench is a first trench, the optical waveguide is a first optical waveguide, and the dielectric layer defines a second trench open to the recess defined by the silicon substrate, and further comprising:
- silicon disposed within the second trench to form a core of a second optical waveguide.

* * * * *